United States Patent
Peltier et al.

(10) Patent No.: US 9,962,420 B2
(45) Date of Patent: *May 8, 2018

(54) COMPOSITIONS AND METHODS FOR TREATING DIABETES, FATTY LIVER, CARDIOPATHIES, INSULIN RESISTANCE, CARBOHYDRATE AND FAT METABOLISM

(71) Applicants: VALBIOTIS, La Rochelle (FR); UNIVERSITE CLERMONT AUVERGNE, Clermont-Ferrand (FR); UNIVERSITE DE LA ROCHELLE, La Rochelle (FR); CNRS, Paris (FR)

(72) Inventors: Sebastien Peltier, Fouras (FR); Pascal Sirvent, Ceyrat (FR); Thierry Maugard, La Jarne (FR)

(73) Assignees: VALBIOTIS, La Rochelle (FR); UNIVERSITE CLERMONT AUVERGNE, Clermont-Ferrand (FR); UNIVERSITE DE LA ROCHELLE, La Rochelle (FR); CNRS, Paris (FR)

( * ) Notice: Subject to any disclaimer, the term of this patent is extended or adjusted under 35 U.S.C. 154(b) by 29 days.

This patent is subject to a terminal disclaimer.

(21) Appl. No.: 14/887,416

(22) Filed: Oct. 20, 2015

(65) Prior Publication Data
US 2016/0106793 A1 Apr. 21, 2016

(30) Foreign Application Priority Data

Oct. 20, 2014 (FR) .................................. 14 60064

(51) Int. Cl.

| | | |
|---|---|---|
| *A61K 36/287* | (2006.01) | |
| *A61K 36/28* | (2006.01) | |
| *A61K 9/00* | (2006.01) | |
| *A61K 9/28* | (2006.01) | |
| *A61K 9/48* | (2006.01) | |
| *A23L 33/105* | (2016.01) | |
| *A61K 36/45* | (2006.01) | |
| *A61K 36/63* | (2006.01) | |
| *A61K 36/67* | (2006.01) | |
| *A61K 45/06* | (2006.01) | |
| *A61K 31/197* | (2006.01) | |
| *A61K 31/4188* | (2006.01) | |
| *A61K 31/4415* | (2006.01) | |
| *A61K 31/4525* | (2006.01) | |
| *A61K 31/455* | (2006.01) | |

(Continued)

(52) U.S. Cl.
CPC .......... *A61K 36/287* (2013.01); *A23L 33/105* (2016.08); *A61K 9/0095* (2013.01); *A61K 9/284* (2013.01); *A61K 9/288* (2013.01); *A61K 9/2813* (2013.01); *A61K 9/2826* (2013.01); *A61K 9/4825* (2013.01); *A61K 31/197* (2013.01); *A61K 31/4188* (2013.01); *A61K 31/4415* (2013.01); *A61K 31/455* (2013.01); *A61K 31/4525* (2013.01); *A61K 31/51* (2013.01); *A61K 31/525* (2013.01); *A61K 31/555* (2013.01); *A61K 31/593* (2013.01); *A61K 31/714* (2013.01); *A61K 33/30* (2013.01); *A61K 36/28* (2013.01); *A61K 36/45* (2013.01); *A61K 36/63* (2013.01); *A61K 36/67* (2013.01); *A61K 45/06* (2013.01); *A23V 2002/00* (2013.01)

(58) Field of Classification Search
CPC .... A61K 2300/00; A61K 36/28; A61K 36/45; A61K 36/67; A61K 2800/42; A61K 2800/45; A61K 2800/52; A61K 2800/522; A61K 8/35; A61K 8/498; A61K 8/11; A61K 8/602; A61K 2800/10; A61K 2800/412; A61K 31/197; A61K 36/53; A61K 31/05; A61K 31/19; A61K 35/614; A61K 36/38; A61K 36/575; A61K 36/752; A61K 31/522; A61K 36/185; A61K 31/133; A61K 36/05; A61K 36/704; A61K 31/4188; A61K 31/4415; A61K 31/4525; A61K 31/455; A61K 31/51; A61K 31/525; A61K 31/555; A61K 31/593; A61K 31/714; A61K 33/30
See application file for complete search history.

(56) References Cited

U.S. PATENT DOCUMENTS

| | | | |
|---|---|---|---|
| 2011/0288125 A1 | 11/2011 | Park | |
| 2012/0148636 A1* | 6/2012 | Berrido | A61K 8/0245 424/400 |
| 2013/0266638 A1 | 10/2013 | Tobia et al. | |

FOREIGN PATENT DOCUMENTS

| | | |
|---|---|---|
| CN | 103271194 | 9/2013 |
| CN | 103652799 | 3/2014 |

(Continued)

OTHER PUBLICATIONS

Chrysanthellum, WikiPhyto, (Mar. 27, 2013), p. 5PP, XP002742311, Extrait de 1 'Internet: URL:http://www.wiki phyto.org/wiki/Chrysanthellum, [extrait le Jul. 14, 2015].

(Continued)

*Primary Examiner* — Debbie K Ware
(74) *Attorney, Agent, or Firm* — Greer, Burns & Crain, Ltd.

(57) ABSTRACT

This disclosure provides compositions formulated in the form of tablets, wafer capsules, gel capsules, sticks, sachets, vials, droppers or in injectable form. The compositions comprise a mixture of: an extract of *Chrysanthellum indicum*, an extract of *Cynara scolymus*, an extract of *Vaccinium myrtillus*, an extract of *Olea europaea*, and pipeline. This disclosure also provides methods of treating pathological disorders of carbohydrate and/or fat metabolism in a patient by administering to the patient the compositions.

20 Claims, 6 Drawing Sheets

(51) Int. Cl.
*A61K 31/51* (2006.01)
*A61K 31/525* (2006.01)
*A61K 31/555* (2006.01)
*A61K 31/593* (2006.01)
*A61K 31/714* (2006.01)
*A61K 33/30* (2006.01)

(56) References Cited

FOREIGN PATENT DOCUMENTS

| | | |
|---|---|---|
| CN | 103719269 | 4/2014 |
| CN | 103750439 | 4/2014 |
| FR | 2908309 | 5/2009 |

OTHER PUBLICATIONS

WikiPhyto: "Poivrier commun", (Aug. 17, 2013), p. 4PP, XP002742312, Extrait de l'Internet: URL:kttp://www.wikiphyto.org/wiki/Poivrier commun, [extrait le Jul. 14, 2015].

Eddouks Mohamed et al., "Antidiabetic Plants Improving Insulin Sensitivity", Journal of Pharmacy and Pharmacology, vol. 6, No. 9, Sep. 2014, pp. 1197-1214.

\* cited by examiner

COMPOSITIONS AND METHODS FOR TREATING DIABETES, FATTY LIVER, CARDIOPATHIES, INSULIN RESISTANCE, CARBOHYDRATE AND FAT METABOLISM

TECHNICAL FIELD

The present invention relates to the prevention and treatment of carbohydrate and/or fat metabolism disorders in humans and animals.

BACKGROUND OF THE INVENTION

Type 2 diabetes, the most common form of diabetes, is a chronic, progressive metabolic disease. It is characterized by chronic hyperglycemia, i.e. an abnormally high concentration of sugar in the blood, and intolerance to carbohydrates. The main cause of this chronic hyperglycemic state is resistance to insulin and inadequate insulin secretion in response to a given metabolic state, but other factors may be involved, as described in Ismail-Beigi F N Engl J Med 2012; 366:1319-27. The main approaches for combating type 2 diabetes should be to reduce the levels of glycemia, to lower the glycated hemoglobin ($HbA_1c$) to a level of less than or equal to 6.5%, and to improve the sensitivity to insulin.

The treatment of type 2 diabetes consists firstly of a change in lifestyle or hygieno-dietetic measures (HDM: the diet, smoking, physical and sports activities). If the HDMs are insufficient, then use should be made of antidiabetic therapeutic agents, generally metformin. However, metformin has many medical contraindications, such as chronic renal insufficiency, acidosis, hypoxia, dehydration, etc. There is thus a substantial paradox for metformin since its prescription is not possible in the case of type 2 diabetic patients presenting with renal insufficiency, but renal insufficiency is one of the common consequences of type 2 diabetes. Other therapeutic agents have been developed, such as dipeptidyl peptidase-IV (DPP-IV) inhibitors, glucagon-like peptide-1 (GLP-1) analogs, thiazolidinediones (TZDs), sulfonylures, glycosidase inhibitors (acarbose, miglitol, voglibose), or sodium glucose co-transporter-2 (SGLT2) inhibitors. However, the correct therapeutic combination is complex since it requires a large number of factors to be taken into consideration, such as the contraindications and the adverse effects, which affect the quality of life of the patients and thus their adherence to the medical treatment. Furthermore, certain therapeutic combinations increase the all-cause mortality, such as the combination of metformin with sulfonylures, as described in Prescrire Int 2015; 24:130-5.

Since HDMs are very rarely adhered to by patients, it is necessary very rapidly to establish a therapeutic treatment with all the adverse effects and contraindications associated with these molecules, and there is at the present time no solution adapted to the care management of type 2 diabetic patients between the HDMs and the establishment of a therapeutic treatment.

Moreover, type 2 diabetic patients have a high risk of cardiovascular morbi-mortality. It is thus also necessary to include in the care management the conventional cardiovascular risk factors especially such as control of the circulating fats, the weight and the arterial pressure. This necessity currently entails the taking of several medicaments of different therapeutic classes simultaneously. However, the combination of drugs may occasionally give rise to serious side reactions, for instance the simultaneous administration of fibrates and statins which increases the risk of myopathy, as described in Denke M A J Manag Care Pharm 2003; 9:17-9.

There is thus a real need for products that can be used both during the attenuated establishment of cardio-metabolic pathologies, characterized by an increase in certain risk factors (carbohydrate disorders, fat disorders, excess weight, inflammation, oxidative stress, arterial hypertension), and during the outbreak of these pathologies, especially type 2 diabetes.

Moreover, there is an urgent need for preventive solutions and medicaments whose "multi-target" mechanism of action has advantages in terms of compliance, tolerance and efficacy. Such products would make it possible to reduce the overall risk of cardio-metabolic diseases and to prevent and treat each dysfunction and/or its consequences taken independently.

SUMMARY OF THE INVENTION

The aim of the invention is to satisfy these various needs by providing compositions that are capable of acting simultaneously on several carbohydrate and fat dysfunctions, which represent both a preventive means and a therapeutic means that is advantageous for preventing and treating cardio-metabolic diseases and complications thereof.

To satisfy its aim, the invention is directed toward compositions comprising at least a mixture of molecules obtained at least from:
*Chrysanthellum indicum*, and
*Cynara scolymus*, and
*Vaccinium myrtillus*,
said mixture of molecules also comprising piperine.

This is a synergistic mixture, the molecules present in the mixture act synergistically.

Extracts of *Chrysanthellum indicum*, extracts of *Cynara scolymus*, extracts of *Vaccinium myrtillus* and piperine have already been described and some of them have been used in nutrition products, but, unexpectedly, the combination of at least one extract of *Chrysanthellum indicum*, with at least one extract of *Cynara scolymus*, an extract of *Vaccinium myrtillus* and piperine leads to surprising results both on carbohydrate metabolism and on fat metabolism in humans and animals.

To satisfy its aim, the invention is also directed toward compositions consisting of at least piperine and particular specific molecules contained in *Chrysanthellum indicum*, *Cynara scolymus* and *Vaccinium myrtillus* (these molecules being natural and/or synthetic), in particular a composition comprising a mixture of at least four molecules, at least one molecule being piperine, at least one molecule being chosen from apigenin 7-O-glucuronide, chrysanthellin A, chrysanthellin B, caffeic acid, luteolin, maritimetin, eriodictyol, isookanin, apigenin, luteolin 7-O-glucoside, maritimein, marein, eriodictyol 7-O-glucoside, flavomarein, apigenin 8-C-α-L-arabinoside-6-C-β-D-glucoside (shaftoside), apigenin 6,8-C-di-β-D-glucopyranoside (vicenin-2), or analogs thereof, and at least one molecule being chosen from a dicaffeoylquinic acid, a sulfo-monocaffeoylquinic acid, luteolin, luteolin 7-O-glucoside, luteolin7-O-glucuronide, apigenin 7-O-glucoside, cynaropicrin or analogs thereof, and at least one molecule being chosen from a monocaffeoylquinic acid, delphinidin 3-galactoside, delphinidin 3-glucoside, cyanidin 3-galactoside, delphinidin 3-arabinoside, cyanidine 3-glucoside, petunidin 3-galactoside, cyanidin 3-arabinoside, petunidin 3-glucoside, peonidin 3-galactoside, petunidin 3-arabinoside, peonidin 3-glucoside, malvidin 3-galactoside, malvidin 3-glucoside, malvidin 3-arabinoside, or analogs thereof.

In the present application, the singular or the plural will be used without preference to denote the compositions according to the invention.

Advantageously, the compositions according to the invention prevent the establishment of chronic hyperglycemia and decrease glycemia, decrease glycated hemoglobin, allow an improvement in the tolerance to ingested carbohydrates, improve the sensitivity to insulin, but are also capable of acting on other cardiovascular risk factors such as dyslipidemia, excess weight and obesity, and arterial tension. In addition, they have few or no side effects with regard to those observed with the existing treatments and those undergoing development.

The invention is thus also directed toward the use of the compositions as nutritional products or health products, especially as medicaments, in particular for preventing and/or combating carbohydrate and fat metabolism disorders in humans and animals.

DETAILED DESCRIPTION OF THE INVENTION

Figure 1:
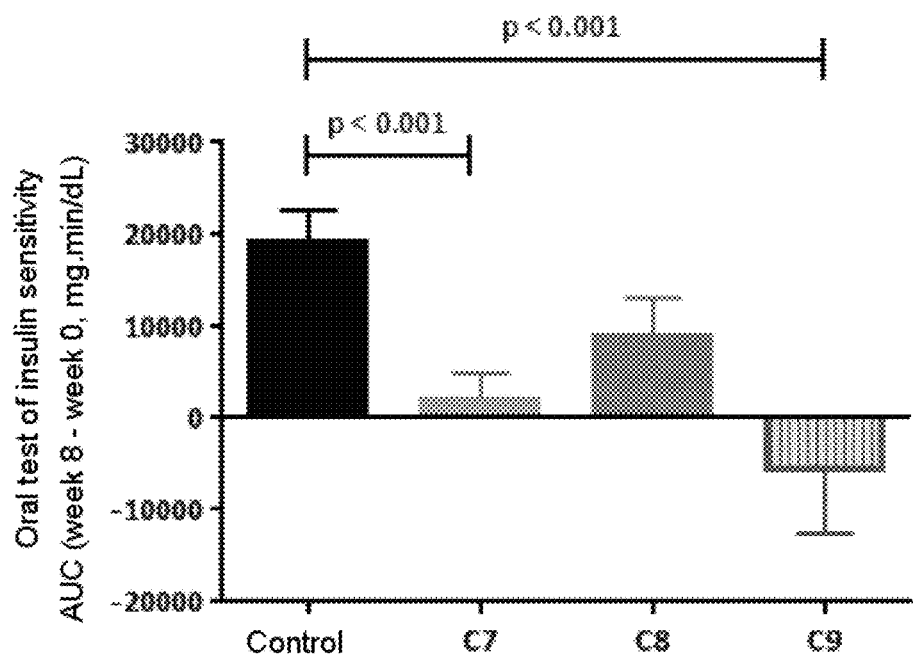
FIG. 1: the results for four compositions of an oral test of sensitivity to insulin corresponding to the results in table 9 (point II.1)

A subject of the invention is a composition comprising at least a mixture of molecules obtained at least from:
*Chrysanthellum indicum*, and
*Cynara scolymus*, and
*Vaccinium myrtillus*,
said mixture of molecules also comprising piperine.

The invention is thus directed toward a composition comprising at least piperine, at least one molecule derived from *Chrysanthellum indicum*, at least one molecule derived from *Cynara scolymus* and at least one molecule derived from *Vaccinium myrtillus*.

In addition to *Chrysanthellum indicum*, *Cynara scolymus*, *Vaccinium myrtillus* and piperine, the composition according to the invention may also contain other compounds, in particular an extract of *Olea europea*. In this case, the composition according to the invention comprises at least one molecule derived from *Chrysanthellum indicum*, at least one molecule derived from *Cynara scolymus*, at least one molecule derived from *Vaccinium myrtillus* and at least one molecule derived from *Olea europea* and piperine.

According to a first embodiment, the composition according to the invention comprises at least:
an extract of *Chrysanthellum indicum*, and
an extract of *Cynara scolymus*, and
an extract of *Vaccinium myrtillus*, and
synthetic piperine and/or an extract of *Piper* containing piperine.

For the purposes of the invention, the term "extract of a plant "X" or of a plant "X" raw material" means at least one molecule, preferentially a set of molecules, obtained from the plant "X" via any suitable process. Mention may be made in particular of aqueous extracts (obtained using an aqueous solvent), alcoholic extracts (obtained using an alcoholic solvent) or using an organic solvent, or using a natural fatty substance or a mixture of natural fatty substances, especially a plant oil or a mixture of plant oils. The term "aqueous solvent" means any solvent consisting totally or partly of water. Mention may thus be made of water itself, aqueous-alcoholic solvents in any proportion or solvents consisting of water and of a compound such as glycerol or propylene glycol in any proportion. Among the alcoholic solvents, mention may be made especially of ethanol.

For the purposes of the invention, the term "plant or plant raw material" means the whole plant or the plant part, including cell cultures, which has not yet undergone a specific treatment and is intended to be included in the manufacture of a plant preparation.

The plant extracts may be obtained via any suitable process, for example, via a process comprising the following steps:
solid/liquid extraction
separation/pressing
filtration
evaporation
drying
optionally incorporation of additives
homogenization
conditioning.

The extract of *Chrysanthellum indicum* is preferably an extract of whole plant or of the aerial parts.

It may in particular be an aqueous-alcoholic or aqueous or subcritical $CO_2$ or subcritical $H_2O$ extract or combined with a heat treatment which is performed by standard heating or under microwave frequency or under ultrasound.

The plant/extract ratio is preferentially between 1/1 and 100/1, in particular between 1/1 and 25/1.

The composition according to the invention, when intended for Human, preferentially comprises an amount of extract of *Chrysanthellum indicum* allowing the administration of at least 0.00001 g, in particular between 0.00001 g and 0.60 g, of extract of *Chrysanthellum indicum* per kg of body weight of the person to whom the composition is administered and per day.

Preferably, the extract of *Chrysanthellum indicum* comprises at least one molecule chosen from apigenin 7-O-glucuronide, chrysanthellin A, chrysanthellin B, caffeic acid, luteolin, maritimetin, eriodictyol, isookanin, apigenin, luteolin 7-O-glucoside, maritimein, marein, eriodictyol 7-O-glucoside, flavomarein, apigenin 8-C-α-L-arabinoside-6-C-β-D-glucoside (shaftoside), apigenin 6,8-C-di-β-D-glucopyranoside (vicenin-2), or analogs thereof. Preferentially, the extract comprises at least apigenin 7-O-glucuronide.

For the purposes of the present invention, the term "analogs" means all compounds having a chemical structure similar to another compound, but differing therefrom by a certain component. It may differ by one or more atoms, functional groups, sub-structures, which are replaced with other atoms, functional groups or sub-structures. Examples that may be mentioned include apigenin 7-O-glucuronide analogs such as apigenin 7-apioglucoside, apigenin 8-C-glucoside (vitexin), apigenin 6-C-glucoside (isovitexin), apigenin 7-O-neohesperidoside, apigenin 7-glucoside, apigenin 7-apioglucoside.

The extract of *Cynara scolymus* is preferably an extract of leaves or roots.

It may in particular be an aqueous-alcoholic or aqueous or subcritical $CO_2$ or subcritical $H_2O$ extract or combined with a heat treatment which is performed by standard heating or under microwave frequency or under ultrasound.

The plant/extract ratio is preferentially between 1/1 and 100/1, in particular between 1/1 and 30/1.

The composition according to the invention, when intended for Human, preferentially comprises an amount of extract of *Cynara scolymus* that allows the administration of at least 0.00001 g, in particular between 0.00001 g and 0.60 g, of extract of *Cynara scolymus* per kg of body weight of the person to whom the composition is administered and per day.

Preferably, the extract of *Cynara scolymus* comprises at least one molecule chosen from a dicaffeoylquinic acid, a sulfo-monocaffeoylquinic acid, luteolin, luteolin 7-O-glucoside, luteolin 7-O-glucuronide, apigenin 7-O-glucoside, cynaropicrin, or analogs thereof.

Preferentially, the extract comprises at least one dicaffeoylquinic acid.

The extract of *Vaccinium myrtillus* is preferably an extract of fruit or leaves.

It may in particular be an aqueous-alcoholic or aqueous or subcritical $CO_2$ or subcritical $H_2O$ extract or combined with a heat treatment which is performed by standard heating or under microwave frequency or under ultrasound.

The plant/extract ratio is preferentially between 1/1 and 200/1, in particular between 1/1 and 60/1.

When it is intended for Human, the composition according to the invention preferentially comprises an amount of extract of *Vaccinium myrtillus* allowing the administration of at least 0.00001 g, in particular between 0.00001 g and 0.60 g, of extract of *Vaccinium myrtillus* per kg of body weight of the person to whom the composition is administered and per day.

Preferably, the extract of *Vaccinium myrtillus* comprises at least one molecule chosen from a monocaffeoylquinic acid, delphinidin 3-galactoside, delphinidin 3-glucoside, cyanidin 3-galactoside, delphinidin 3-arabinoside, cyanidin 3-glucoside, petunidin 3-galactoside, cyanidin 3-arabinoside, petunidin 3-glucoside, peonidin 3-galactoside, petunidin 3-arabinoside, peonidin 3-glucoside, malvidin 3-galactoside, malvidin 3-glucoside, malvidin 3-arabinoside, or analogs thereof. Preferentially, the extract comprises at least one monocaffeoylquinic acid.

The piperine present in the composition according to the invention may be contained in an extract of *Piper* or may be a synthetic piperine.

The topological formula of piperine is as follows:

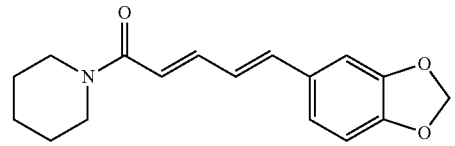 [SMILES: O=C(/C=C/C=C/c1ccc2c(c1)OCO2)N1CCCCC1]

The composition according to the invention, when intended for Human, preferentially comprises an amount of piperine allowing the administration of at least 0.001 mg, in particular between 0.001 mg and 166 mg, of piperine per kg of body weight of the person to whom the composition is administered and per day.

If the piperine is contained in an extract of *Piper*, the mixture of the composition according to the invention comprises said extract. The extract of *Piper* is preferentially an extract of *Piper nigrum*, of *Piper aduncum* and/or of *Piper longum*.

The extract of *Piper* is preferably an extract of fruit or leaves.

It may in particular be an aqueous-alcoholic or aqueous or subcritical $CO_2$ or subcritical $H_2O$ extract or combined with a heat treatment that is performed by standard heating or under microwave frequency or under ultrasound.

The plant/extract ratio is preferentially between 1/1 and 10000/1, in particular between 1/1 and 200/1.

The extract preferentially comprises at least 1% of piperine by weight relative to the total weight of the extract.

Thus, the mixture of the composition according to the invention preferentially comprises:
- at least piperine, and
- at least one molecule chosen from apigenin 7-O-glucuronide, chrysanthellin A, chrysanthellin B, caffeic acid, luteolin, maritimetin, eriodictyol, isookanin, apigenin, luteolin 7-O-glucoside, maritimein, marein, eriodictyol 7-O-glucoside, flavomarein, apigenin 8-C-α-L-arabinoside-6-C-β-D-glucoside (shaftoside), apigenin 6,8-C-di-β-D-glucopyranoside (vicenin-2), or analogs thereof, preferably apigenin 7-O-glucuronide, and
- at least one molecule chosen from a dicaffeoylquinic acid, a sulfo-monocaffeoylquinic acid, luteolin, luteolin 7-O-glucoside, luteolin 7-O-glucuronide, apigenin 7-O-glucoside, cynaropicrin, or analogs thereof, preferentially a dicaffeoylquinic acid, and
- at least one molecule chosen from a monocaffeoylquinic acid, delphinidin 3-galactoside, delphinidin 3-glucoside, cyanidin 3-galactoside, delphinidin 3-arabinoside, cyanidin 3-glucoside, petunidin 3-galactoside, cyanidin 3-arabinoside, petunidin 3-glucoside, peonidin 3-galactoside, petunidin 3-arabinoside, peonidin 3-glucoside, malvidin 3-galactoside, malvidin 3-glucoside, malvidin 3-arabinoside, or analogs thereof, preferentially at least one monocaffeoylquinic acid.

In addition to the extracts of *Chrysanthellum indicum, Cynara scolymus* and *Vaccinium myrtillus*, and piperine, the mixture according to the invention may also contain other compounds, in particular an extract of *Olea europaea*.

The extract of *Olea europaea* is preferentially an extract of leaves or fruit.

It may in particular by an aqueous-alcoholic or aqueous or subcritical $CO_2$ or subcritical $H_2O$ extract or combined with a heat treatment that is performed by standard heating or under microwave frequency or under ultrasound.

The plant/extract ratio is preferentially between 1/1 and 200/1, in particular between 1/1 and 60/1.

The composition according to the invention, when intended for Human, preferentially comprises an amount of extract of *Olea europaea* allowing the administration of at least 0.00001 g, in particular between 0.00001 g and 0.60 g, of extract of *Olea europaea* per kg of body weight of the person to whom the composition is administered and per day.

Preferably, the extract of *Olea europaea* comprises at least one molecule chosen from oleuropein and hydroxytyrosol, or analogs thereof.

By mixture within the meaning of the invention, we mean the combination of substances (extracts and/or molecules) in solid, liquid or gas that can interact chemically or not.

The mixture according to the invention is obtained via any process known to those skilled in the art. It may be obtained by simple mixing of the constituents.

Preferentially the ratio of the extract of *Chrysanthellum indicum*/extract of *Cynara scolymus*/extract of *Vaccinium myrtillus*/piperine in the mixture is between 0.01/0.01/0.01/0.0001 and 10/10/10/10.

According to one variant, in addition to the mixture consisting of several plant extracts or in place of the mixture consisting of several plant extracts, the mixture of molecules of the composition according to the invention may comprise at least:
    a single extract obtained from a mixture of at least two plants chosen from *Chrysanthellum indicum, Cynara scolymus* and *Vaccinium myrtillus* and *Piper* and optionally,
    one extract of *Chrysanthellum indicum* if the mixture of plants of the single extract does not comprise *Chrysanthellum indicum,*
    one extract of *Cynara scolymus* if the mixture of plants of the single extract does not comprise *Cynara scolymus,*
    one extract of *Vaccinium myrtillus* if the mixture of plants of the single extract does not comprise *Vaccinium myrtillus,*
    piperine or an extract of *Piper* if the mixture of plants of the single extract does not comprise *Piper.*

Preferentially, when the composition comprises a single extract, it comprises:
    a single extract obtained from at least *Chrysanthellum indicum, Cynara scolymus* and *Vaccinium myrtillus* and *Piper*, and/or
    piperine and a single extract obtained from at least *Chrysanthellum indicum, Cynara scolymus* and *Vaccinium myrtillus.*

For the purposes of the invention, the term "single extract obtained from several plants "X" or plant "X" raw materials" means a set of molecules obtained from a mixture of at least two plants "X" via any suitable process. Mention may be made in particular of aqueous extracts (obtained using an aqueous solvent), alcoholic extracts (obtained using an alcoholic solvent) or using an organic solvent, or using a natural fatty substance or a mixture of natural fatty substances, especially a plant oil or a mixture of plant oils. The term "aqueous solvent" means any solvent consisting totally or partly of water. Mention may thus be made of water itself, aqueous-alcoholic solvents in any proportion or solvents consisting of water and of a compound such as glycerol or propylene glycol in any proportion. Among the alcoholic solvents, mention may be made especially of ethanol.

For the purposes of the invention, the term "plant or plant raw material" means the whole plant or the plant part, including cell cultures, which has not yet undergone a specific treatment and is intended to be included in the manufacture of a plant preparation.

The single extract of a mixture of plants "X" may be obtained via any suitable process, for example via a process comprising the following steps:
    solid/liquid extraction
    separation/pressing
    filtration
    evaporation
    drying
    optionally incorporation of additives
    homogenization
    conditioning.

Use is preferentially made of the whole plant or the aerial parts of *Chrysanthellum indicum* as plant raw material to obtain the single extract. The single extract is preferentially prepared from at least 0.1% of whole plant or of the aerial parts of *Chrysanthellum indicum* by weight relative to the total weight of the mixture of plants used for preparing the single extract.

Use is preferentially made of the leaves or roots of *Cynara scolymus* as plant raw material for obtaining the single extract. The single extract is preferentially prepared from at least 0.1% of leaves or roots of *Cynara scolymus* by weight relative to the total weight of the mixture of plants used for preparing the single extract.

Use is preferentially made of the fruit or leaves of *Vaccinium myrtillus* as plant raw material for obtaining the single extract. The single extract is preferentially prepared from at least 0.1% of fruit or leaves of *Vaccinium myrtillus* by weight relative to the total weight of the mixture of plants used for preparing the single extract.

If the single extract is obtained from a mixture of plants comprising *Piper*, the fruit or leaves of *Piper nigrum*, of *Piper aduncum* and/or of *Piper longum* are preferentially used as plant raw material for obtaining the single extract. The single extract is preferentially prepared from at least 0.0001% of fruit or leaves of *Piper nigrum*, and/or of *Piper aduncum* and/or of *Piper longum* by weight relative to the total weight of the mixture of plants used for preparing the single extract.

The single extract may thus comprise, in addition to the other molecules, at least oleuropein, hydroxytyrosol, and/or at least piperine.

Preferably, the single extract comprises:
    at least one molecule chosen from apigenin 7-O-glucuronide, chrysanthellin A, chrysanthellin B, caffeic acid, luteolin, maritimetin, eriodictyol, isookanin, apigenin, luteolin 7-O-glucoside, maritimein, marein, eriodictyol 7-O-glucoside, flavomarein, apigenin 8-C-α-L-arabinoside-6-C-β-D-glucoside (shaftoside), apigenin 6,8-C-di-β-D-glucopyranoside (vicenin-2), or analogs thereof, preferentially apigenin 7-O-glucuronide, and at least one molecule chosen from a dicaffeoylquinic acid, a sulfo-monocaffeoylquinic acid, luteolin, luteolin 7-O-glucoside, luteolin 7-O-glucuronide, apigenin 7-O-glucoside, cynaropicrin, or analogs thereof, preferentially a dicaffeoylquinic acid, and at least one molecule chosen from a monocaffeoylquinic acid, delphinidin 3-galactoside, delphinidin 3-glucoside, cyanidin 3-galactoside, delphinidin 3-arabinoside, cyanidin 3-glucoside, petunidin 3-galactoside, cyanidin 3-arabinoside, petunidin 3-glucoside, peonidin 3-galactoside, petunidin 3-arabinoside, peonidin 3-glucoside, malvidin 3-galactoside, malvidin 3-glucoside, malvidin 3-arabinoside, or analogs thereof, preferentially at least one monocaffeoylquinic acid, and and piperine.

In addition to *Chrysanthellum indicum*, *Cynara scolymus* and *Vaccinium myrtillus*, the single extract of the composition according to the invention may also preferentially be obtained from *Olea europaea*. Use is preferably made of the leaves or fruit of *Olea europaea* as plant raw material for obtaining the single extract. The single extract is preferentially prepared from at least 0.1% of leaves or fruit of *Olea europaea* by weight relative to the total weight of the mixture of plants used for preparing the single extract.

A particularly suitable embodiment is a composition comprising a single extract obtained from *Chrysanthellum indicum*, *Cynara scolymus*, *Vaccinium myrtillus*, *Piper* and *Olea europaea*.

The composition according to the invention comprising a single extract, when intended for Human, preferentially comprises an amount of single extract corresponding to an administration of at least 0.00001 g, in particular between 0.00001 g and 0.60 g of single extract per kg of body weight of the person to whom the composition is administered and per day.

The composition according to the invention comprising plant extracts and/or one or more single extracts thus comprises:
at least one molecule chosen from apigenin 7-O-glucuronide, chrysanthellin A, chrysanthellin B, caffeic acid, luteolin, maritimetin, eriodictyol, isookanin, apigenin, luteolin 7-O-glucoside, maritimein, marein, eriodictyol 7-O-glucoside, flavomarein, apigenin 8-C-α-L-arabinoside-6-C-β-D-glucoside (shaftoside), apigenin 6,8-C-di-β-D-glucopyranoside (vicenin-2), or analogs, preferentially apigenin 7-O-glucuronide, and from a dicaffeoylquinic acid, a sulfo-monocaffeoylquinic acid, luteolin, luteolin 7-O-glucoside, luteolin 7-O-glucuronide, apigenin 7-O-glucoside, cynaropicrin, or analogs thereof, preferentially a dicaffeoylquinic acid, and at least one molecule chosen from a monocaffeoylquinic acid, delphinidin 3-galactoside, delphinidin 3-glucoside, cyanidin 3-galactoside, delphinidin 3-arabinoside, cyanidin 3-glucoside, petunidin 3-galactoside, cyanidin 3-arabinoside, petunidin 3-glucoside, peonidin 3-galactoside, petunidin 3-arabinoside, peonidin 3-glucoside, malvidin 3-galactoside, malvidin 3-glucoside, malvidin 3-arabinoside, or analogs thereof, preferentially at least one monocaffeoylquinic acid, and at least piperine, and optionally, preferentially at least one molecule chosen from oleuropein, hydroxytyrosol, or analogs thereof.

According to another aspect, the invention is also directed toward a composition comprising a mixture of at least four molecules, these molecules possibly being synthetic molecules and/or natural molecules, especially derived from plant raw materials:

at least one molecule being chosen from apigenin 7-O-glucuronide, chrysanthellin A, chrysanthellin B, caffeic acid, luteolin, maritimetin, eriodictyol, isookanin, apigenin, luteolin 7-O-glucoside, maritimein, marein, eriodictyol 7-O-glucoside, flavomarein, apigenin 8-C-α-L-arabinoside-6-C-β-D-glucoside (shaftoside), apigenin 6,8-C-di-β-D-glucopyranoside (vicenin-2), or analogs thereof, and at least one molecule being chosen from a dicaffeoylquinic acid, a sulfo-monocaffeoylquinic acid, luteolin, luteolin 7-O-glucoside, luteolin 7-O-glucuronide, apigenin 7-O-glucoside, cynaropicrin, or analogs thereof, and at least one molecule being chosen from a monocaffeoylquinic acid, delphinidin 3-galactoside, delphinidin 3-glucoside, cyanidin 3-galactoside, delphinidin 3-arabinoside, cyanidin 3-glucoside, petunidin 3-galactoside, cyanidin 3-arabinoside, petunidin 3-glucoside, peonidin 3-galactoside, petunidin 3-arabinoside, peonidin 3-glucoside, malvidin 3-galactoside, malvidin 3-glucoside, malvidin 3-arabinoside, or analogs thereof, and at least piperine, and At least one of the first three molecules is a synthetic molecule. Indeed, independently of piperine which may be synthetic or natural, at least one of the other molecules is a synthetic molecule.

In addition to these at least four molecules, the mixture may also comprise at least one molecule chosen from oleuropein, hydroxytyrosol, or analogs thereof, these molecules possibly being synthetic or natural molecules.

According to a particularly suitable variant, the mixture comprises at least one dicaffeoylquinic acid, apigenin 7-O-glucuronide, a monocaffeoylquinic acid, piperine and oleuropein. The mixture of molecules of the composition according to the invention may consist exclusively of a dicaffeoylquinic acid, apigenin 7-O-glucuronide, a monocaffeoylquinic acid, piperine and oleuropein.

According to other variants, the compositions of the invention may comprise a mixture of extract(s) and molecule(s) of interest presented in this application (for example an extract of *Chrysanthellum indicum* and at least one molecule being chosen from a dicaffeoylquinic acid, a sulfo-monocaffeoylquinic acid, luteolin, luteolin 7-O-glucoside, luteolin 7-O-glucuronide, apigenin 7-O-glucoside, cynaropicrin, or analogs thereof, and at least one molecule being chosen from a monocaffeoylquinic acid, delphinidin 3-galactoside, delphinidin 3-glucoside, cyanidin 3-galactoside, delphinidin 3-arabinoside, cyanidin 3-glucoside, petunidin 3-galactoside, cyanidin 3-arabinoside, petunidin 3-glucoside, peonidin 3-galactoside, petunidin 3-arabinoside, peonidin 3-glucoside, malvidin 3-galactoside, malvidin 3-glucoside, malvidin 3-arabinoside, or analogs thereof, and at least piperine).

The compositions according to the invention in their different variants may consist exclusively of the elements described (plant extracts and/or single extract(s) or mixture of at least four molecules), or else may also comprise at least one additional element (products, molecules, extracts, active principles, excipients, etc.) added in addition to the plant extracts and/or the single extract(s) or of the mixture of at least four molecules, said additional element possibly being chosen from:

the following vitamins: B1, B2, B3, B5, B6, B8, B9, B12 C, A, D, E, K1 and K2;

the following compounds: obeticholic acid, corosolic acid, polyunsaturated fatty acids of the omega 6 and/or omega 3 family, orotic acid, pangamic acid, para-aminobenzoic acid, amygdalin, beta-glucans, carnitine, dimethylglycine, imeglimin, isoflavones, L-arginine, oxytocin, pectin, pyridoxamine, resveratrol, viniferin, L-citrulline; the following trace elements and minerals: arsenic, boron, calcium, copper, iron, fluorine, iodine, lithium, manganese, magnesium, molybdenum, nickel, phosphorus, selenium, vanadium, zinc;

the following microconstituents of non-essential nature: conjugated linolenic acid, lipoic add, carotenoids, carnitine, choline, coenzyme Q10, phytosterols, polyphenols of the tannin and lignan family, taurine;

fructo-oligosaccharides, galacto-oligosaccharides;

lactic acid-fermenting bacteria;

yeasts, for example red rice yeast (*Monascus purpureus*);

muschroom, for example maitake;

products derived from insects that are compatible with the food and pharmaceutical sector;

marijuana and hashish;

coating agents: for example hypromellose, microcrystalline cellulose, stearic acid, talc, sucrose, shellac, povidone, beeswax;

flavors: for example natural flavor of blueberry or natural flavor of strawberry;

acidifying agents such as malic acid;

antiagglomerating agents: for example silicon dioxide or magnesium stearate;

thickeners such as xanthan gum, colloidal silica, fatty acid mono- and diglycerides;

stabilizers such as calcium phosphate;

emulsifiers such as soybean lecithin;

fillers such as corn starch;

excipients: for example microcrystalline cellulose, magnesium stearate or dicalcium phosphate.

The compositions according to the invention may also comprise one or more extracts of at least one of the following plant raw materials and/or one or more molecules contained in at least one of the following plant materials and/or the single extract may also be obtained from at least one of the following plant raw materials: *Abelmoschus esculentus, Abies Alba, Abies balsamea, Abies sibirica, Acacia nilotica, Acacia senegal, Achillea millefollium, Achyranthes bidentata, Acmella oleracea, Actaea racemosa, Actinidia chinensis, Actinidia deliciosa, Adansonia digitata, Adiantum capillus-veneris, Aesculus hippocastanum, Afromomum melegueta, Agathosma betulina, Agathosma crenulata, Agathosma serratifolia, Agrimonia eupatoria, Ajuga reptans, Albizia julibrissin, Alchemilla vulgaris, Alliara petiolata, Allium ampeloprasum, Allium cepa, Allium sativum, Allium schoenoprasum, Allium ursinum, Alnus glutinosa, Aloe ferox, Aloe vera, Aloysia citriodora, Alpinia galanga, Alpinia hainanensis, Alpinia officinarum, Alpinia oxyphylla, Althaea officinalis, Ammi visnaga, Amorphophallus konjac, Ananas comosus, Andographis paniculata, Anemarrhena asphodeloides, Anethum graveolens, Angelica archangelica, Angelica dahurica, Angelica pubescens, Angelica sinensis, Antennaria diocia, Anthriscus cerefolium, Anthyllis vulneraria, Aphanizomenon flos-aquae Ralfs, Apium graveolens, Arachis hypogaea, Aralia elata, Arctium lappa, Arctium minus, Argania spinosa, Armorica rustanica, Artemisia dracunculus, Artemesia vulgaris, Ascophyllum nodosum, Aspalathus linearis, Asparagus officinalis, Astragalus membranaceus, Atractylodes lancea, Atractylodes macrocephala, Auracaria columnaris, Avena staiva, Ayahuasca, Baccharis genistelloides, Bacopa monnierri, Ballota nigra, Bambusa bambos, Bellis perennis, Berberis vulgaris, Beta vulgaris, Betula alleghaniensis, Betula pendula, Betula pubescens, Bixa orellana, Borago officnalis, Boswellia serrata, Brassica napus, Brassica nigra, Brassica oleracea, Brassica rapa, Bupleurum chinense, Calendula officinalis, Calluna vulgaris, Camellia sinsensis, Capsella bursa-pastoris, Capsicum annuum, Carex arenaria, Carica papaya, Carlina acaulis, Carphephorus odoratissmus, Carpinus betulus, Carthamus tinctorius, Carum carvi, Cassia fistula, Castanea sativa, Centaurea centaurium, Centaurea cyanus, Centaurium erythraea, Centella asiatica, Cerasus vulgaris, Ceratonia silliqua, Chaenomelum nobile, Chlorella vulgaris, Chondrus crispus, Chrysanthellum indicum, Cichorium intybus, Cinchona officinalis, cinchona pubescens, Cinnamomum camphora, Cinnamomum cassia, Cinnamomum verum, Cistanche salsa, Cistus incanus, Citrus aurantium, Citrus limon, Citrus maxima, Citrus medica, Citrus myrtifolia, Citrus reticulata blanco, Citrus sinsensis, Citrus paradisi, Clinopodium vulgore, Cnicus benedictus, Cochlearia officinalis, Cocos nucifera, Codonopsis pilosula, Coffea canephora, Coix lacryma-jobi* var. *mayyuen Stapf, Cola acuminata, Cola ballayi cornu, Cola nitida, Combretum micranthum, Commiphora mukul, Conyza canadensis, Coriandrum sativum, Cornus officinalis, Corylus avellana, Corymbia citriodora, Crataegus laevigata, Craetegus monogyna, Crithmum maritimum, Crocus sativus, Cucumis melo, Cucurbita pepo, Cuminum cyminum, Cupressus sempervirens, Cuscuta chinensis, Cyamopsis tetragonoloba, Cyathula officinalis, Cyclanthera pedata, Cydonia oblonga, Cymbopogon martini, Cymbopogon nardus, Cymbopogon winterianus, Cynara cardunculus, Cyperus rotundus, Daucus carota, Dendranthema grandiflorum, Desmodium adscendens, Dimocarpus Iongan, Dioscorea oppostifolia, Dioscorea villosa, Diospyros kaki Thunb., Dunaliella saliena, Echinacea augustifolia, Echinacea pallida, Echinacea purpurea, Eloegnus rhamnoides, Alettaria cardamomum, Eleutherococcus senticosus, Elymus repens, Epiobium augustifolium, Epilobium parviflorum, Equisetum arvense, Erica cinerea, Erica tetralix, Eriobotrya japonica, Eriodictyon californicum, Erodium cicutarium, Eryngium campestre, Eschscholzia californica, Eucalyptus dives Schauer, Eucalyptus globulus, Eucalyptus radiata, Eucalyptus smithii F. Muell, Eucommia ulmoides, Eugenia uniflora, Eugenia jambolana, Euphrasia stricta D. Wolff, Euterpe oleracea, Fagopyrum esculentum Moench, Follopia japonica, Ferula assa-foetida, Ficus carica, Filipendula ulmaria, Foeniculum vulgare Mill., Forsythia suspensa, Fragaria dodonei Ard., Frangula purshiana Cooper, Fraxinus excelsior, Fraxinus ortus, Fucus serratus, Fucus vesiculosus, Fumaria officinalis, Galeopsis segetum Neck., Galium odotorum, Galium verum, Gardenia jasminoides J. Ellis, Gastrodia elata Blume, Gelidium corneum J.V. Lamouroux, Gentiana lutea, Geranium robertianum, Geum urbanum, Ginkgo biloba, Glycine max, Glycyrrhiza glabra, Glycyrrhiza uralensis, Gracilaria gracilis, Grindelia camporum Greene, Grindelia robusta Nutt., Grindelia squarrosa Dunal, Gymnema sylvestris, Haematococcus pluviaolis, Hamamemis virginiana, Harpagophytum procumbens, Harpagophytum zeyheri Decne., Hedeoma pluegioides Pers., Helianthus annuus, Helienthus tuberosus, Helichrysum arenarium, Helichrysum stoechas, Herniara glabra, Hibiscus sabdariffa, Hieracium pilosella, Himanthalia elongata, Hordeum vulgare, Houttuynia cordata Thunb., Huperzia serrata, Hyssopus officinalis, Ilex paraguariensis A. St.-Hill, Illicum verum, Impatients balsamina, Inula britannica, Inula hele-* nium, Jasminum grandiflorum, Jasmium officinale, Juniperus communis, Justicia adhatoda, Kavalama urens, Krameria lappacea, Lagerstroemia speciosa, Laminaria digitata, Laminaria hyperborea, Lamium album, Larix deciduo, Larix occidentalis, Laurus nobilis, Lavandula augustofolia, Lavandula latifolia, Ledum palustre, Leonurus cordioca, Lepidium meyenii Walp., Lepidium sativum, Lespedeza capitata, Levisticum officinale, Lindera aggregata, Linus usitatissimum, Liquidambar styraciflua, Lotus corniculatus, Lycium barbarum, Lycium chinense, Lycopersicon esculentum, Lycopodium clavatum, Lycopus europaeus, Lythrum salicaria, Macadamia ternifolia F. muell, Macrocystis pyrifera, Magnolia officinalis, Malpighia glabra, Malus pumila, Malus domestica, Malus sylvestris, Malva sylvestris, Mangifera indica, Maranta arundinacea, Marrubium vulgare, Marsdenia cundurango, Marsdenia sylvestris, Mastocarpus stellatus, Matricaria chamomilla, Medicago sativa, Melaleuca alternifolia, Melaleuca cajuputi Powell, Melaleuca leucadendra, Melaleuca quinquenrvia, Melaleuca viridiflora, Melilotus altissimus Thuill., Melilotus officinalis, Mentha arvensis, Menthaxpiperita, Menyanthes trifoliata, Mesembryanthemum crystallinum, Monarda didyma, Morinda citrifolia, Morinda officinalis, Morus alba, Morus nigra, Murraya koenigii, Musaxparadisiaca, Myrciaria dubia, Myristica flagrans Houtt., Myroxylon balsamum, Myrtus communis, Nardostachys jatamansi, Nasturtium officinale R. Br., Nelumbo nucifera Gaertn., Nepeta cataria, Nepeta tenuifolia Benth., Nigella sativa, Ocimum basilicum, Oenothera biennis, Ononis spinosa, ophiopogon japonicus, Opuntia ficus-indica, Origanum compactum Benth., Origanum majorana, Origanum vulgare, Orthosiphon aristatus, Oryza sativa, Paeonia lactiflora, Paeoniaxsuffruticosa Andrews, Palmaria palmata, Panax ginseng, Panax quinquefolius, Panicum miliacium, Papaver rhoeas, Parietaria officinalis, Passiflora edulis Sims, Pastinaca sativa, Paullinia cupana Kunth, Pelargonium graveolens, Perilla frutescens, Persea americana, Persicaria bistorta, Persicaria maculosa Gray, Petroselinum crispum, Peucadanum ostruthium, Peumus boldus Molina, Phaseolus vulgaris, Phellodendron amurense, Photinia melancarpa, Phyllanthus emblica, Physalis alkekengi, Phymatolithon calcareum, Picea abies, Pimento dioca, Pimenta racemosa, Pimpinella anisum, Pimpinella major, Pimpinella saxfraga, Pinus mugo Turra, Pinus pinaster Aiton, Pinus sylvestris, Pistacia lentiscus, Plantago arenaria, Plantago lanceolata, Plantago major, Plantago ovata, Platycodon grandiflorus, Plectranthus barbatus Andrews, Pogostemom cablin, Polygala senega, Polygala sibirica, Polygala tenuifolia Willd., Polygonum aviculare, Populus nigra, Populus tremula, Populus tremuloides, Porphyra umbilicalis, Portulaca oleracea, Potentilla erecta, Primula veris, Prunella vulgaris, Prunus africana, Prunus armeniaca, Ribes nigrum, Ribes uva-crispa, Rosa canina, Rosa gallica, Rosa moschata, Rosa rubiginosa, Rosmarinus officinalis, Rubus caesius, Rubus fruticosus, Rubus idaeus, Rumex actetosa, Rumex acetosella, Rumex crispus, Rumex patienta, Ruscus aculeatus, Sachharina japonica, Saccharina latissima, Salix alba, Salix fragilis, Salix pentandra, Salix purpurea, Salvia officinalis L., Salvia officinalis subsp. lavandulifolia Gams, Salvia sclarea, Sambucus nigra, Sanguisorba officinalis, Sanicula elata Buch.-Ham. Ex D. Don, Santalum album, Santolina chamaecyparissus, Saposhnikovia divaricata, Sargassum fusiforme, Satureja hortensis, Satureja montana, Saussurea costus, Scrophularia ningpoensis Helmsl., Scutellaria baicalensis Georgi, Secale cereale, Sedum acre, Sedum roseum, Senna alexandrina Mill., Senna obustifolia, Smilax cordifolia Humb. & Bonpl., Smilax glabra Roxb., Smilax officinalis Kunth, Smilax purhampuy Ruiz, Smilax purhampuy Ruiz, Smilax regelli Killip and C.V. Morton, Smilax vanillidora Apt, Solanum melongena, Solanum tuberosum, Solidago virgaurea, Sorbus aucuparia, Spatholobus suberctus Dunn., Spinacia oleracea, Spirulina major Kiutzing, Spirulina maxima Geitler, Spirulina platensis Geitler, Stavhys officinalis, Stemmacantha carthamoides Dittrich, Stypholobium japonicum, Syzgium aromaticum, Tagetes erecta, Tamarindus indica, Tanacetum parthemium, Terminalia chebula Retz., Theobroma cacao, Thymus saturejoides Coss., Thymus serpyllum, Thymus vulgaris, Thymus zygis, Tilia cordata Mill., Tilia platyphyllos Scop., Tilia tomentosa Moench, Tilia euopaea, Tribulus terrestris, Trichosanthes kirilowii Maxim., Trifolium arvense, Trifolium campestre Schreb., Trifolium pratense, Trifolium repens, Trigonella caerulea, Trigonella foenum-graecum, Tricitum aestivum, Tricitum durum Desf., Tricitum spelta L., Tricitum turgidum, Tropaeolum majus, Turnera diffusa Willd., Ulmus glabra Huds., Ulmus glabra Huds., Ulmus pumila, Ulmus rubra Muhl., Ulva lactuca, Uncaria gambir Roxb., Uncaria rhynchophylla Miq., Uncaria tomentosa DC., Undaria pinnatifida Suringar, Urtica dioca, Urtica urens, Vaccinium macrocarpon, Vaccinium oxycoccos, Vaccinium vitis-idae, Valeriana jatamansi Jones, Valeriana officinalis, Vanilla planifolia Jacks, Verbascum densiflorum Bertol., Verbascum thapsus, Verbena officinalis, Veronica officinalis, Viburnum opulus, Vigna angularis Ohwi & H. Ohashi, Vinca major, Vinca minor, Viola palustris, Viola tricolor, Vitex agnus-castus, Vitex trifolia, Vitis vinifera, Zea mays, Zingiber officinale Roscoe, Ziziphusjujuba Mill.

The compositions according to the invention may be in any form, especially in the form of powder, gel, emulsion or in liquid form, in particular in the form of tablets, wafer capsules, gel capsules, sticks, sachets, vials, droppers or in injectable form.

The compositions according to the invention may be used as nutrition products or health products in particular as medicaments.

The term "nutrition product" means any product having a nutritional and/or physiological effect, this especially comprising food supplements, foods, dietetic products, etc. These products may in particular be administered via the oral, gastric or venous route.

The term "health product" means any product which has a beneficial effect on health, in prevention or treatment, whether this effect is physiological or pharmacological, especially medicaments, pharmaceutical products. These products may in particular be administered via the oral, gastric, venous or cutaneous route.

The compositions according to the invention may be used for preventing and/or combating carbohydrate and/or fat metabolism disorders in Human or animals.

They are particularly suitable for preventing and/or combating type 2 diabetes in Human or animals. Specifically, they make it possible to prevent the establishment of chronic hyperglycemia, to decrease fasting glycemia and glycated hemoglobin, circulating and hepatic triglycerides, body mass and fat mass, to increase HDL cholesterol ("good cholesterol") and to improve the tolerance to ingested carbohydrates and insulin sensitivity. They may be used preventively in the treatment of type 2 diabetes and as a first line treatment, during the establishment of HDMs, thus making it possible to defer the implementation of the usual oral antidiabetic molecules. They are also particularly suitable for treating type 2 diabetes and its complications, non-alcoholic steatohepatitis (NASH) especially, alone or in combination with other pharmacological treatments.

The compositions according to the invention may also be used for preventing and/or combating type 1 diabetes and/or non-alcoholic fatty liver diseases, in particular non-alcoholic steatohepatitis (NASH), and/or cardiovascular pathologies, in particular coronary cardiopathies, cerebrovascular diseases, peripheral arteriopathies, deep vein thrombosis, and/or pathologies associated with insulin resistance, for example Alzheimer's disease (Bedse G et al. Front Neurosci 2015; 9:204).

For such uses, the compositions according to the invention may be used in combination with at least one antidiabetic therapeutic agent chosen from biguanides including metformin, dipeptidyl peptidase-IV (DPP-IV) inhibitors, glucagon-like peptide-1 (GLP-1) analogs, thiazolidinediones (TZDs), sulfonylureas, rapid and slow insulins, glycosidase inhibitors (acarbose, miglitol, voglibose), sodium glucose co-transporter-2 (SGLT2) inhibitors, molecules of the fibranor family such as elafibranor, or molecules targeting nuclear receptors and especially the ROR (α, β, γ) receptors and Rev-Erb (α, β) receptors.

The compositions according to the invention may also be used for acting on other cardiovascular risk factors or metabolic syndrome.

In particular, the compositions according to the invention may be used for preventing and/or combating dyslipidemia. They especially have a hypocholesterolemiant effect and make it possible to reduce the total level of cholesterol, the level of LDL cholesterol, the circulating triglycerides and the hepatic triglycerides. They also have inhibitory activity on HMG-CoA reductase.

For such uses, the compositions according to the invention may be used in combination with a hypolipemiant therapeutic agent chosen from: statins, fibrates, nicotinic acid, ion-exchange resins, cholesterol absorption inhibitors, omega-3 polyunsaturated fatty acids, tiadenol, and FXR (Farnesoid X Receptor) nuclear receptor agonists.

Finally, the compositions according to the invention may be used specifically for preventing or combating obesity and excess weight and/or metabolic syndrome and/or pathological arterial tension problems.

The invention is now illustrated by examples of extracts and of compositions, and also by results of tests demonstrating the efficacy of the compositions according to the invention, these examples and tests not being limiting.

I. EXAMPLES

Example 1: Example of Dry Extract of *Chrysanthellum indicum*

The aerial parts of the fresh or dry plant are subjected to mechanical grinding until a coarse powder is obtained. This powder is then subjected to a maceration step for 10 to 24 hours at room temperature in a 70/10 water/ethanol mixture, and the mix obtained is then subjected to continuous leaching at 50° C. in a percolator with a 70/10 water/ethanol mixture, the plant/extract ratio being 3/1. The extract obtained is then subjected to liquid/liquid washes using a nonpolar organic solvent such as dichloromethane or trichloromethane. After concentrating by evaporation at low pressure at 35° C., a liquid is obtained, which is lyophilized for 24 hours to give a beige-colored powder that is soluble in a water/alcohol mixture. This powder (dry extract) may be used directly or may be mixed in a suitable solvent before use.

Example 2: Example of Dry Extract of *Vaccinium myrtillus*

Blueberry in powder form obtained from *Vaccinium myrtillus* fruit is subjected to a maceration step for 10 to 24 hours at room temperature in a 30/50 water/ethanol mixture and the mix obtained is then subjected to continuous leaching at 50° C. in a percolator with a 30/50 water/ethanol mixture, the plant/extract ratio being 10/1. The extract obtained is then subjected to liquid/liquid washes using a nonpolar organic solvent such as dichloromethane or trichloromethane. After concentrating by evaporation at low pressure at 35° C., a liquid is obtained, which is lyophilized for 24 hours to give a violet-colored powder which is soluble in a water/alcohol mixture.

Example 3: Example of Dry Extract of *Cynara scolymus*

Artichoke in powder form obtained from leaves of *Cynara scolymus* is subjected to a step of maceration for 10 to 24 hours at room temperature in water, and the mix obtained is then subjected to continuous leaching at 50° C. in a percolator with water, the plant/extract ratio being 2/1. The extract obtained is then subjected to liquid/liquid washes using a nonpolar organic solvent such as dichloromethane or trichloromethane. After concentrating by evaporation at low pressure at 35° C., a liquid is obtained which is lyophilized for 24 hours to give a beige-colored powder that is soluble in water.

Example 4: Example of Dry Extract of *Olea europaea*

Air-dried whole olive tree leaves are ground at −80° C. using a knife mill to obtain a fine and uniform powder. The powder obtained is then subjected to a maceration step for 10 to 24 hours in a 70/30 water/ethanol mixture. The step is performed in a closed system with a nitrogen sparge at room temperature, or under a microwave power of 800 watts or under an ultrasound frequency of 20 kHz for 2×3 min. The mix obtained is then subjected to continuous leaching at 50° C. in a percolator with a 70/30 water/ethanol mixture, the plant/extract ratio being 10/1. The extract obtained is then subjected to liquid/liquid washes using a nonpolar organic solvent such as dichloromethane or trichloromethane. After concentrating by evaporation at low pressure at 35° C., a liquid is obtained, which is lyophilized for 24 hours to give a green-colored powder in a water/alcohol mixture.

Example 5: Examples of Single Extract

*Chrysanthellum* in powder form obtained from the aerial parts of *Chrysanthellum indicum*, and artichoke in powder form obtained from *Cynara scolymus* leaves, and blueberry in powder form obtained from *Vaccinium myrtillus* fruit, and *Piper nigrum* fruit powder, and olive tree in powder form obtained from *Olea europaea* leaves are subjected to a step of maceration for 10 to 24 hours at room temperature in a 40/60 water/ethanol mixture, and the mix obtained is then subjected to continuous leaching at 50° C. in a percolator with a 40/60 water/ethanol mixture, the mixture of plants/single extract ratio being from 4 to 6/1. The extract obtained is then subjected to liquid/liquid washes using a nonpolar organic solvent such as dichloromethane or trichloromethane. After concentrating by evaporation at low pressure at 35° C., a liquid is obtained, which is lyophilized for 24 hours to give a violet-colored powder that is soluble in a water/alcohol mixture.

Example 6: Example of a Composition According to the Invention in the Form of Tablets, Comprising Four Plant Extracts The composition of example 6 is in the form of tablets that may be administered orally. It comprises, expressed as weight percentages, relative to the total weight of the composition, 30.1% of dry extract of aerial parts of *Chrysanthellum indicum*, 30.1% of dry extract of *Cynara scolymus* leaves, 3.0% of dry extract of *Vaccinium myrtillus* fruit and 0.3% of dry extract of *Piper nigrum* fruit. It also comprises excipients, in particular microcrystalline cellulose and magnesium stearate.

The composition for three tablets is indicated in Table 1 below.

TABLE 1

Example of composition in tablet form

| List of ingredients | For three tablets |
| --- | --- |
| Dry extract of aerial parts of *Chrysanthellum indicum* | 600 mg |
| Dry extract of *Cynara scolymus* leaves | 600 mg |
| Dry extract of *Vaccinium myrtillus* fruit | 60 mg |
| Dry extract of *Piper nigrum* fruit | 6 mg |
| Microcrystalline cellulose | 700 mg |
| Magnesium stearate | 26 mg |

Example 7: Example of a Composition According to the Invention in the Form of Gel Capsules, Comprising Five Plant Extracts The composition of example 7 is in the form of gel capsules that may be administered orally. It comprises, expressed as weight percentages relative to the total weight of the composition, 37.0% of dry extract of aerial parts of *Chrysanthellum indicum*, 37.0% of dry extract of *Cynara scolymus* leaves, 3.7% of dry extract of *Vaccinium myrtillus* fruit, 0.004% of dry extract of *Piper nigrum* fruit, and 22.2% of dry extract of *Olea europaea* leaves.

The composition for three gel capsules is indicated in Table 2 below.

TABLE 2

Example of composition in the form of gel capsules

| List of ingredients | For three gel capsules |
| --- | --- |
| Dry extract of aerial parts of *Chrysanthellum indicum* | 200 mg |
| Dry extract of *Cynara scolymus* leaves | 200 mg |
| Dry extract of *Vaccinium myrtillus* fruit | 20 mg |
| Dry extract of *Piper nigrum* fruit | 0.02 mg |
| Dry extract of *Olea europaea* leaves | 120 mg |

Example 8: Example of a Composition According to the Invention in the Form of Tablets, Comprising Five Plant Extracts The composition of example 8 is in the form of tablets that may be administered orally. It comprises, as weight percentages relative to the total weight of the composition, 22.0% of dry extract of the aerial parts of *Chrysanthellum indicum*, 22.0% of dry extract of *Cynara scolymus* leaves, 2.2% of dry extract of *Vaccinium myrtillus* fruit, 13.2% of dry extract of *Olea europaea* leaves, and 0.2% of dry extract of *Piper nigrum* fruit. The composition also comprises, in addition to the mixture, zinc, vitamins B9, PP, B5, H, B12, D, B6, B2, B2 and chromium. It also comprises excipients, in particular dicalcium phosphate, microcrystalline cellulose and magnesium stearate.

The composition for one tablet is indicated in Table 3 below.

TABLE 3

Example of composition in the form of tablets

| List of ingredients | In mg for one tablet | Reference nutritional value for one tablet |
| --- | --- | --- |
| Dry extract of aerial parts of *Chrysanthellum indicum* | 220.0 | — |
| Dry extract of *Cynara scolymus* leaves | 220.0 | — |
| Dry extract of *Vaccinium myrtillus* fruit | 22.0 | — |
| Dry extract of *Olea europaea* leaves | 132.0 | — |
| Dry extract of *Piper nigrum* fruit | 2.0 | — |
| Dicalcium phosphate | 198.0 | — |
| Microcrystalline cellulose | 153.44 | — |
| Magnesium stearate | 20.0 | — |
| Zinc bisglycinate | 12.99 | 33% |
| Vitamin B9 - folic acid | 7.30 | 33% |
| Vitamin PP - nicotinamide | 5.30 | 33.1% |
| Vitamin B5 - calcium pantothenate | 2.24 | 33.3 |
| Vitamin H - biotin | 1.66 | 33.2% |
| Vitamin B12 | 0.83 | 33.2% |
| Vitamin D3 | 0.64 | 32% |
| Vitamin B6 - pyridoxine hydrochloride | 0.56 | 32.9% |
| Vitamin B1 - thiamine hydrochloride | 0.48 | 32.7% |
| Vitamin B2 - riboflavin | 0.45 | 32.1% |
| Chromium picolinate | 0.11 | 32.5% |

Example 9: Example of a Composition According to the Invention in the Form of Tablets, Comprising Four Plant Extracts The composition of example 9 is in the form of tablets that may be administered orally. It comprises, expressed as weight percentages relative to the total weight of the composition, 23.9% of dry extract of *Chrysanthellum indicum* whole plants, 23.9% of dry extract of *Cynara scolymus* leaves, 23.9% of dry extract of *Vaccinium myrtillus* fruit and 0.2% of dry extract of *Piper nigrum* fruit. The composition also comprises vitamin B1, vitamin B3, pantothenic acid (vitamin B5), zinc and chromium. As excipients, it comprises microcrystalline cellulose and dicalcium phosphate. As coating agents, it comprises talc, sugar, shellac, povidone and beeswax.

The composition for three tablets is indicated in Table 4 below.

TABLE 4

Example of composition in tablet form

| List of ingredients | For three tablets | Reference nutritional value for three tablets |
|---|---|---|
| Dry extract of *Vaccinium myrtillus* fruit | 600 mg | — |
| Dry extract of *Chrysanthellum indicum* whole plants | 600 mg | — |
| Dry extract of *Cynara scolymus* leaves | 600 mg | — |
| Dry extract of *Piper nigrum* fruit | 5 mg | — |
| Vitamin B1 | 1.1 mg | 100% |
| Vitamin B3 (inositol hexanicotinate) | 16 mg (nicotinic acid) | 100% |
| Pantothenic acid (vitamin B5) | 6 mg | 100% |
| Zinc (zinc bisglycinate) | 5 mg | 50% |
| Chromium (chromium picolinate) | 40 µg | 100% |
| Microcrystalline cellulose | 600 mg | — |
| Dicalcium phosphate | 75 mg | — |

Example 10: Example of a Composition According to the Invention in the Form of a Powder to be Reconstituted in Water, Conditioned in the Form of Sticks, Comprising Four Plant Extracts The composition of example 10 is in the form of a powder to be reconstituted in water, conditioned in the form of sticks that may be administered orally. It comprises, expressed as weight percentages relative to the total weight of the composition, 36.3% of dry extract of *Chrysanthellum indicum* whole plants, 24.2% of dry extract of *Cynara scolymus* roots, 36.3% of dry extract of *Vaccinium myrtillus* fruit and 2.4% of dry extract of *Piper longum* fruit. The composition also comprises vitamin B1, vitamin B3, pantothenic acid (vitamin B5), zinc and chromium. As flavor, it comprises a natural blueberry flavor. As acidifying agent, it comprises malic acid. As antiagglomerating agent, it comprises silicon dioxide, as thickener, xanthan gum, and as stabilizer, calcium phosphate.

Its composition is indicated in Table 5 below.

TABLE 5

Example of composition in the form of powder to be reconstituted in water and conditioned in the form of sticks

| List of ingredients | For three sticks | Reference nutritional value for three sticks |
|---|---|---|
| Dry extract of *Vaccinium myrtillus* fruit | 1500 mg | — |
| Dry extract of *Chrysanthellum indicum* whole plants | 1500 mg | — |
| Dry extract of *Cynara scolymus* roots | 1000 mg | — |
| Dry extract of *Piper longum* fruit | 100 mg | — |
| Vitamin B1 | 1.1 mg | 100% |
| Vitamin B3 (inositol hexanicotinate) | 16 mg (nicotinic acid) | 100% |
| Pantothenic acid (vitamin B5) | 6 mg | 100% |
| Zinc (zinc bisglycinate) | 5 mg | 50% |
| Chromium (chromium picolinate) | 40 µg | 100% |

Example 11: Example of a Composition According to the Invention in the Form of a Powder to be Reconstituted in Water, Conditioned in the Form of Sticks The composition of example 11 is in the form of a powder to be reconstituted in water, conditioned in the form of sticks that may be administered orally. It comprises, expressed as weight percentages relative to the total weight of the composition, 37.0% of dry extract of aerial parts of *Chrysanthellum indicum*, 37.0% of dry extract of *Cynara scolymus* leaves, 3.7% of dry extract of *Vaccinium myrtillus* fruit, 0.2% of dry extract of *Piper nigrum* fruit, and 22.2% of dry extract of *Olea europaea* leaves. The composition also comprises vitamin B12 and chromium. As flavor, it comprises a natural strawberry flavor. As antiagglomerating agent, it comprises silicon dioxide. This composition does not comprise any antiagglomerating agent and thickener.

The composition of such a product is indicated in Table 6 below.

TABLE 6

Example of composition in the form of powder to be reconstituted in water and conditioned in the form of sticks

| List of ingredients | For three sticks | Reference nutritional value for three sticks |
|---|---|---|
| Dry extract of *Vaccinium myrtillus* fruit | 120 mg | — |
| Dry extract of aerial parts of *Chrysanthellum indicum* | 1200 mg | — |
| Dry extract of *Cynara scolymus* leaves | 1200 mg | — |
| Dry extract of *Piper nigrum* fruit | 6 mg | — |
| Dry extract of *Olea europaea* leaves | 720 mg | — |
| Vitamin B3 (inositol hexanicotinate) | 2.5 µg | 100% |
| Chromium (chromium picolinate) | 20 µg | 50% |

Example 12: Example of a Composition According to the Invention in the Form of Gel Capsules The composition of example 12 is in the form of gel capsules that may be administered orally. It comprises, expressed as weight percentages relative to the total weight of the composition, 31.6% of dry extract of the aerial parts of *Chrysanthellum indicum*, 47.4% of dry extract of *Cynara scolymus* roots, 15.8% of dry extract of *Vaccinium myrtillus* fruit and 2.6% of piperine. The composition also comprises vitamin B3 and zinc. As emulsifier, It comprises soybean lecithin derived from non-GMO production, as thickeners, colloidal silica and fatty acid mono- and diglycerides. The capsule is a fish gelatin, with glycerol and a colorant, red iron oxide.

The composition of such a product is indicated in Table 7 below.

TABLE 7

Example of composition in the form of gel capsules

| List of ingredients | For two gel capsules | Reference nutritional value for two gel capsules |
|---|---|---|
| Dry extract of Vaccinium myrtillus fruit | 100 mg | — |
| Dry extract of the aerial parts of Chrysanthellum indicum | 200 mg | — |
| Dry extract of Cynara scolymus roots | 300 mg | — |
| Piperine | 15 mg | — |
| Vitamin B3 | 8 mg (nicotinic acid) | 50% |
| Zinc (zinc gluconate) | 10 mg | 100% |

Example 13: Example of a Composition According to the Invention in the Form of Gel Capsules The composition of example 13 is in the form of gel capsules that may be administered orally. It comprises, expressed as weight percentages relative to the total weight of the composition, 10.4% of dry extract of *Chrysanthellum indicum* whole plants, 20.7% of dry extract of *Cynara scolymus* leaves, 62.1% of dry extract of *Vaccinium myrtillus* leaves and 2.6% of piperine. As filler, it comprises corn starch. As antiagglomerating agents, it comprises silicon dioxide and magnesium stearate. The gel capsule is of plant origin.

The composition of such a product is indicated in Table 8 below.

TABLE 8

Example of composition in the form of gel capsules

| List of ingredients | For one gel capsule | Reference nutritional value for one gel capsule |
|---|---|---|
| Dry extract of Vaccinium myrtillus leaves | 300 mg | — |
| Dry extract of Chrysanthellum indicum whole plants | 50 mg | — |
| Dry extract of Cynara scolymus leaves | 100 mg | — |
| Piperine | 15 mg | — |

Example 14: Example of a Composition According to the Invention in the Form of Gel Capsules Comprising a Single Extract The composition of example 14 is in the form of gel capsules that may be administered orally. It comprises a single aqueous-alcoholic extract of a powder mixture obtained from the aerial parts of *Chrysanthellum indicum*, from *Cynara scolymus* leaves, from *Vaccinium myrtillus* fruit, from *Piper nigrum* fruit and from *Olea europaea* leaves. The ratio between the three plants is 1/1/0.1/0.0001/0.6.

The single extract of the mixture of plants may be obtained via any suitable process, for example via a process comprising the following steps:
solid/liquid extraction
separation/pressing
filtration
evaporation
drying
optionally incorporation of additives
homogenization
conditioning.

Example 15: Example of a Composition According to the Invention in the Form of Tablets Comprising Synthetic Molecules or Molecules Obtained from Plant Raw Materials The composition of example 15 is in the form of film-coated tablets that may be administered orally. It comprises as active substance for one tablet: 50 mg of apigenin 7-O-glucuronide, 50 mg of dicaffeoylquinic acid, 100 mg of monocaffeoylquinic acid, 10 mg of piperine and 250 mg of oleuropein. The other components used as excipients are: pregelatinized starch, sodium carboxymethyl starch (type A), stearic acid, povidone K90, anhydrous colloidal silica.

The active substances may be synthetic or derived from plant raw materials or derived from plant extracts by purification by high-performance liquid-phase chromatography.

II. IN VIVO EVALUATION OF THE EFFICACY OF THE COMPOSITION in vivo experiments on mice were performed to demonstrate the effects of the compositions according to the invention, in particular on fasting glycemia, glycated hemoglobin, carbohydrate tolerance, insulin sensitivity, body mass and fat mass, and on the circulating and hepatic fats. Similarly, molecular biology evaluations were performed. Finally, the compositions were compared with reference pharmacological treatments already on the market or undergoing development.

The experiments were performed on db/db mice. db/db mice have a mutation of the leptin receptors inducing a cell signaling dysfunction of the latter. The leptin receptors are highly expressed in the hypothalamus. Mice having a mutation of these receptors cannot efficiently regulate their energy stores. This results in high insulinemia from the first days of life (10-14 days), and obesity from 3 to 4 weeks with an increase in glycemia. These mice are insulin resistant, hypertriglyceridemic and glucose-intolerant. They constitute a pertinent and predictive model especially for studying insulin sensitivity, triglyceridemia, type 2 diabetes and one of its complications, non-alcoholic steatohepatitis (NASH) (Aileen J F King Br J Pharmacol 2012; 166(3):877-894; Sanches S C et al. Biomed Res Int 2015).

II.1 Tests A

The experimental time was nine weeks with a "run-in" of one week followed by eight weeks of supplementation with the plant extracts and a composition X. The male mice were ten weeks old at the start of the treatment.

Nine compositions X were tested. These compositions were directly incorporated into the rodents' feed, which makes it possible to ensure its "multi-target" efficacy and its large-scale use, since intravenous or intraperitoneal injections are limited to a small number of people, given their mode of administration. This also avoids daily force-feeding, which alters various physiological processes.

The compositions tested were as follows:
C1: *Chrysanthellum indicum* (whole plant)+piperine (1% and 0.1% of the feed, respectively);
C2: *Cynara scolymus* (leaves)+piperine (1% and 0.1% of the feed, respectively);

C3: *Vaccinium myrtillus* (fruits)+piperine (1% and 0.1% of the feed, respectively);

C4: *Chrysanthellum indicum* (whole plant)+*Cynara scolymus* (leaves)+*Vaccinium myrtillus* (fruits)+piperine (1%, 1%, 1% and 0.1% of the feed, respectively);

C5: piperine (0.1% of the feed, respectively);

C6: *Chrysanthellum indicum* (whole plant)+*Cynara scolymus* (leaves)+*Vaccinium myrtillus* (fruits) (1%, 1% and 1% of the feed, respectively);

C7: *Chrysanthellum indicum* (whole plant)+*Cynara scolymus* (leaves)+*Vaccinium myrtillus* (fruits)+piperine (1%, 1%, 1%, 0.001% of the feed, respectively);

C8: *Olea europaea* (leaves) (0.6% of the feed, respectively);

C9: *Chrysanthellum indicum* (whole plant)+*Cynara scolymus* (leaves)+*Vaccinium myrtillus* (fruits)+piperine+*Olea europaea* (leaves) (1%, 1%, 1%, 0.001%, 0.6% of the feed, respectively).

The term "piperine" means either synthetic piperine or a standardized *Piper* extract containing 95% piperine. For the other plants, they are dry extracts obtained from plant raw materials.

The experiments took place in several steps. Consequently several "ad libitum control" groups were made. The results obtained from these groups were pooled. Compositions C1, C2, C3, C4, C5, C8 and C9 induced a similar decrease in feed intake. Consequently, a "Per Fed control" group, i.e. a group consuming the same daily amount of food as groups C1, C2, C3, C4, C5, C8 and C9, was made so as to be able to compare the results for an equivalent feed intake.

The experimental evaluations focused especially on:
Measurement of the body mass;
Measurement of the fasting glycemia;
The change in glycemia during an oral test of carbohydrate tolerance. After force-feeding with starch (3 g/kg) in the fasted state, the change in glycemia in response to starch was measured in the tail by biopsy just before the force-feeding (t0) and then after 30, 60, 90 and 120 minutes. The area under the curve (AUC) was calculated. An increase in the AUC reflects a carbohydrate intolerance, a decrease reflects an improvement in carbohydrate tolerance.

For compositions C7 to C9, an insulin sensitivity test was also performed. This test consisted of an intraperitoneal injection of insulin (2 U/kg) in the fasted state. The change in glycemia in response to the insulin injection was measured in the tail by biopsy just before the injection (t0) and then after 30, 60, 90 and 120 minutes. The area under the curve (AUC) was calculated. A decrease in the AUC reflects a better response to the insulin injection and thus an improvement in the insulin sensitivity. Conversely, an increase in the AUC reflects poorer insulin sensitivity and thus insulin resistance.

The evaluations presented were performed just before the supplementation (t=0) and at the end of supplementation (t=8 weeks).

The results obtained are presented in tables:
Table 9 for the effect on the insulin sensitivity after eight weeks of treatment,
Table 10 for the effect on the fasting glycemia after eight weeks of treatment,
Table 11 for the effect on the carbohydrate tolerance after eight weeks of treatment,
Table 12 for the effect on the body mass after eight weeks of treatment.

Insulin Sensitivity

TABLE 9

Effect of the compositions on the insulin sensitivity after eight weeks of treatment

| Compositions | AUC (week 8 − week 0, in mg × min/dL) (mean ± SEM) |
|---|---|
| ad libitum control | 19 186 ± 3460 |
| C7 | 2082 ± 2082 ** |
| C8 | 8970 ± 2959 |
| C9 | −6520 ± 4685 ** |

Mean values ± SEM.
ad libitum control, n = 20; C7, n = 11; C8, n = 10; C9, n = 9.
Composition versus control, Student's t test for unpaired data,
** p < 0.01.

The results presented in Table 9 are also illustrated in FIG. 1. These results show a very significant and large effect of compositions C7 and C9 on the insulin sensitivity. The improvement in insulin sensitivity with compositions C7 and C9 according to the invention is particularly advantageous in prevention and in treatment of type 2 diabetes and complications thereof. Specifically, insulin resistance is one of the major mechanisms of progression of type 2 diabetes (Samuel V T et al. Cell 2012; 148:852-71). Moreover, by acting on this parameter, compositions C7 and C9 according to the invention are particularly suitable in other pathologies in which one of the major causes is insulin resistance. This is particularly the case for one of the complications of type 2 diabetes, non-alcoholic steatohepatitis (NASH; Samuel V T et al. Cell 2012; 148:852-71), and Alzheimer's disease (Bedse G et al. Front Neurosci 2015; 9:204).

Fasting Glycemia

TABLE 10

Effect of the compositions on the fasting glycemia after eight weeks of treatment

| Compositions | Fasting glycemia (in mg/dL) |
|---|---|
| ad libitum control | 534 ± 10 |
| Per Fed control | 518.2 ± 38 |
| C1 | 410.4 ± 33 * |
| C2 | 448 ± 34 |
| C3 | 384 ± 40 * |
| C4 | 335 ± 38 ** |
| C5 | 449 ± 11 |
| C6 | 536 ± 15 |
| C7 | 571 ± 14 * |
| C8 | 400 ± 61 |
| C9 | 220 ± 78 ** |

Mean values ± SEM.
ad libitum control, n = 32; Per Fed control, n = 10; C1, n = 9; C2, n = 9; C3, n = 9; C4, n = 8; C5, n = 9; C6, n = 14; C7, n = 12; C8, n = 12; C9, n = 9.
Composition versus control, Student's t test for unpaired data,
* p < 0.05,
** p < 0.01.

Compositions C1, C2, C3, C4, C5, C8 and C9 brought about a decrease in feed intake. Consequently, a Per Fed group consuming the same amount of food was made. The results show that the calorie restriction imposed on the animals had no effect on the fasting glycemia (comparison of ad libitum control versus Per Fed control). Compositions C1, C3, C4 and C9 induced a significant decrease in fasting glycemia, the most pronounced effect being observed with compositions C4 (1% *Chrysanthellum indicum*, 1% *Cynara scolymus*, 1% *Vaccinium myrtillus*, 0.1% piperine) and C9

(1% *Chrysanthellum indicum*, 1% *Cynara scolymus*, 1% *Vaccinium myrtillus*, 0.001% piperine, 0.6% *Olea europaea*).

Composition C6 (1% *Chrysanthellum indicum*, 1% *Cynara scolymus*, 1% *Vaccinium myrtillus*) had no effect on the fasting glycemia. The addition of piperine (0.1%), although it (C5) induced no significant decrease in the fasting glycemia, to the C6 combination to obtain the C4 combination, made it possible, surprisingly, to significantly and strongly lower the fasting glycemia. Similarly, the addition of *Olea europaea* (0.6%; C8) to the C7 combination (1% *Chrysanthellum indicum*, 1% *Cynara scolymus*, 1% *Vaccinium myrtillus*, 0.001% piperine) to obtain composition C9 also made it possible to strongly lower the glycemia to a level virtually similar to that of nondiabetic mice.

Carbohydrate Tolerance

TABLE 11

Effect of the compositions on the carbohydrate tolerance after eight weeks of treatment

| Compositions | AUC (week 8 – week 0, in mg × min/dL) (mean ± SEM) |
|---|---|
| ad libitum control | 10 954 ± 2000 |
| Per Fed control | 20 355 ± 6554 |
| C1 | 3367 ± 3039 * |
| C2 | 1901 ± 3949 * |
| C3 | −2418 ± 3260 ** |
| C4 | −11 537 ± 4168 ** |
| C5 | 3610 ± 2086 * |
| C6 | 13 068 ± 3064 |
| C7 | 8639 ± 2844 |
| C8 | −8889 ± 5436 ** |
| C9 | −24 568 ± 10 440 ** |

Mean values ± SEM.
ad libitum control, n = 22; Per Fed control, n = 10; C1, n = 9; C2, n = 8; C3, n = 10; C4, n = 8; C5, n = 9; C6, n = 14; C7, n = 12; C8, n = 10; C9, n = 9.
AUC: "area under the curve".
Composition versus control, Student's t test for unpaired data,
* $p < 0.05$,
** $p < 0.01$.

Compositions C1, C2, C3, C4, C5, C8 and C9 brought about a decrease in feed intake. Consequently, a Per Fed group consuming the same amount of food was made. The results show that the calorie restriction imposed on the animals had no effect on the carbohydrate tolerance (comparison of ad libitum control versus Per Fed control). Compositions C1, C2, C3, C4, C5, C8 and C9 induced a significant decrease in the AUC, which reflects an improvement in the carbohydrate tolerance. The most pronounced effect is obtained with the combinations C4 and C9.

Body Mass

TABLE 12

Effect of the compositions on the body mass after eight weeks

| Compositions | Body mass (in g, mean ± SEM) |
|---|---|
| ad libitum control | 36.9 ± 1.2 |
| Per Fed control | 30.6 ± 1.2 |
| C1 | 33.9 ± 2.4 |
| C2 | 37.4 ± 2.2 * |
| C3 | 37.0 ± 2.7 * |
| C4 | 36.3 ± 1.7 * |
| C5 | 32.7 ± 1.5 |
| C6 | 29.3 ± 1.8 *** |
| C7 | 34.5 ± 1.6 |

TABLE 12-continued

Effect of the compositions on the body mass after eight weeks

| Compositions | Body mass (in g, mean ± SEM) |
|---|---|
| C8 | 26.9 ± 2.0 |
| C9 | 25.0 ± 2.1 * |

Mean values ± SEM.
ad libitum control, n = 34; Per Fed control, n = 10; C1, n = 9; C2, n = 9; C3, n = 9; C4, n = 8; C5, n = 9; C6, n = 14; C7, n = 12; C8, n = 10; C9, n = 9.
Composition versus control, Student's t test for unpaired data,
* $p < 0.05$,
** $p < 0.01$,
*** $p < 0.0001$.

Compositions C1, C2, C3, C4, C5, C8 and C9 brought about a decrease in feed intake. Consequently, a Per Fed group consuming the same amount of food was made. The results show that the calorie restriction imposed on the animals induced a significant decrease in body mass (comparison of ad libitum control versus Per Fed control, $p < 0.05$). Compositions C2, C3, C4, C6 and C9 also induced a significant decrease in body mass. Whereas the combination C6 had no effect on the fasting glycemia, it induced a large and significant decrease in body mass, giving it advantageous properties in the prevention and treatment of obesity. The combination C9 had the most pronounced effect.

Synergistic Effect

Moreover, the synergistic effect was evaluated according to the method of Colby S R described in "Calculation of the synergistic and antagonistic responses of herbicide combinations" *Weeds*, 1967, 15:20-22. This method was especially used in patent EP03812880. For each combination, the synergistic factor was calculated. A factor >1 indicates the existence of a synergistic effect. A factor <1 indicates the existence of an antagonist. The calculations performed are:

Expected degree of efficacy=$A+B-(A*B/100)$

Synergistic factor(SF)=$(1*$observed degree of efficacy (%))/expected degree of efficacy (%)

The calculations related to the following combinations:
Calculation of SF for the 1% *Chrysanthellum indicum*/1% *Cynara scolymus*/1% *Vaccinium myrtillus*/0.1% piperine combination (composition C4) in which A=1% *Chrysanthellum indicum*/1% *Cynara scolymus*/1% *Vaccinium myrtillus* (C6) and B=piperine (C5);
Calculation of SF for the 1% *Chrysanthellum indicum*/1% *Cynara scolymus*/1% *Vaccinium myrtillus*/0.001% piperine/0.6% *Olea europaea* combination (composition C9) in which A=1% *Chrysanthellum indicum*/1% *Cynara scolymus*/1% *Vaccinium myrtillus*/0.001% piperine (composition C7) and B=0.6% *Olea europaea* (composition C8).

Table 13 below gives the results for the combination C6+C5=C4.

TABLE 13

Synergistic factors for the combination C6 + C5 = C4

| | Observed degree of efficacy (in % of the control group) | | | Expected degree of efficacy | Synergistic factor |
|---|---|---|---|---|---|
| | C6 | C5 | C4 | with C4 | |
| Fasting glycemia after eight weeks of treatment | +2.6% | −13.3% | −35.3% | −11.0% | 3.20 |

TABLE 13-continued

Synergistic factors for the combination C6 + C5 = C4

| | Observed degree of efficacy (in % of the control group) | | | Expected degree of efficacy with C4 | Synergistic factor |
|---|---|---|---|---|---|
| | C6 | C5 | C4 | | |
| Oral test of carbohydrate tolerance, AUC (week 8 – week 0) | +9.5% | −82.3% | −156.7% | −82.3% | 1.94 |

Figure 2:
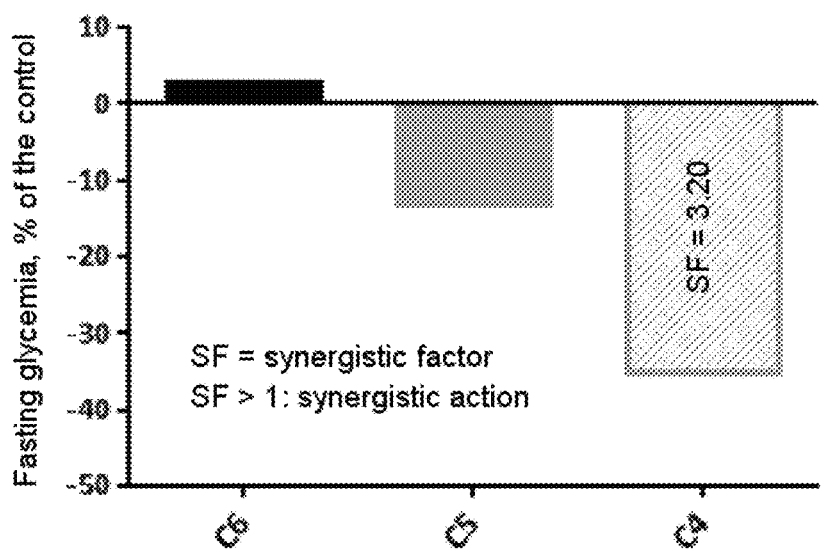
FIG. 2: the results demonstrating the synergistic effect afforded by a composition according to the invention, these results corresponding to the results of table 13 (point II.1) for fasting glycemia.
Figure 3:
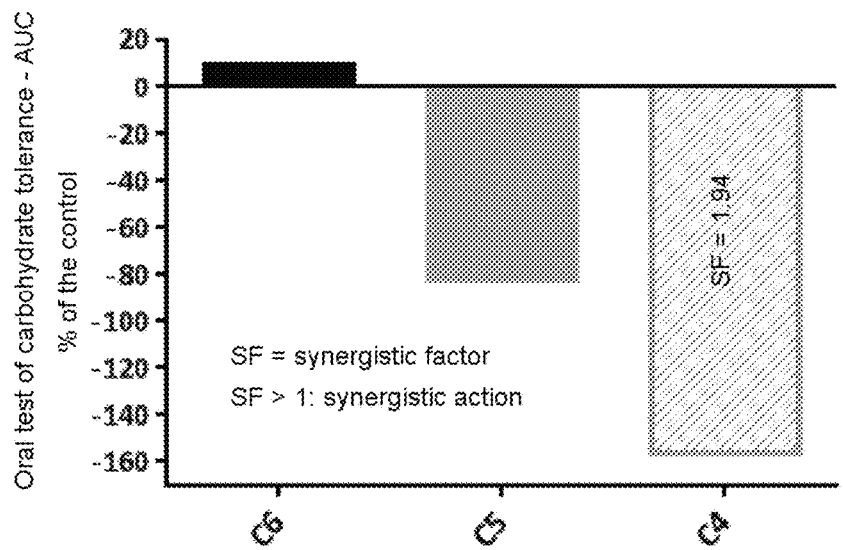
FIG. 3: the results demonstrating the synergistic effect afforded by a composition according to the invention, these results corresponding to the results of table 13 (point II.1) for carbohydrate tolerance.

The results presented in Table 13 are illustrated in FIGS. 2 and 3. A large synergistic effect with composition C4 according to the invention is demonstrated, both on the fasting glycemia and on the carbohydrate tolerance (AUC).

Table 14 below gives the results for the combination C7+C8=C9.

TABLE 14

Synergistic factors for the combination C7 + C8 = C9

| | Observed degree of efficacy (in % of the control group) | | | Expected degree of efficacy with C9 | Synergistic factor |
|---|---|---|---|---|---|
| | C7 | C8 | C9 | | |
| Fasting glycemia after eight weeks of treatment | +5.7% | −26.1% | −59.4% | −21.9% | 2.71 |
| Oral test of carbohydrate tolerance, AUC (week 8 – week 0) | +4.6% | −204.5% | −388.7% | −209.3% | 1.86 |
| Oral test of insulin sensitivity, AUC (week 8 – week 0) | −89.1% | −53.2% | −129.3% | −94.9% | 1.36 |

Figure 4:
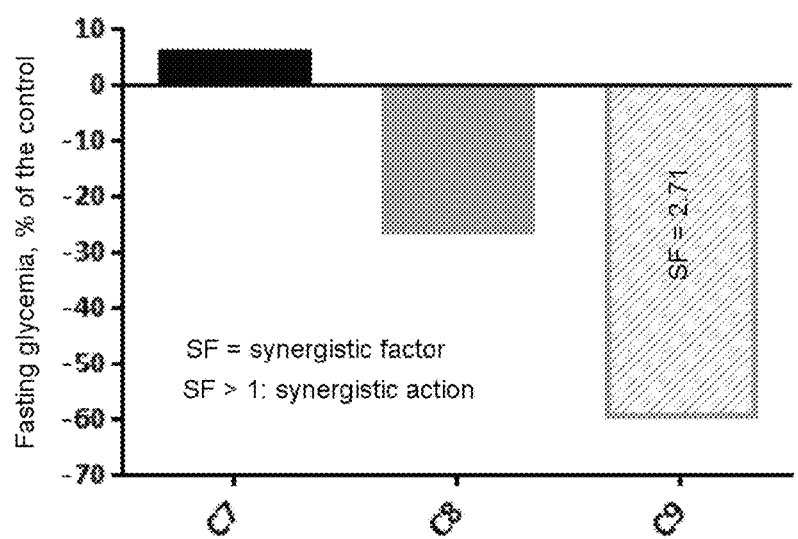
FIG. 4: the results demonstrating the synergistic effect afforded by a composition according to the invention, these results corresponding to the results of table 14 (point II.1) for fasting glycemia.
Figure 5:
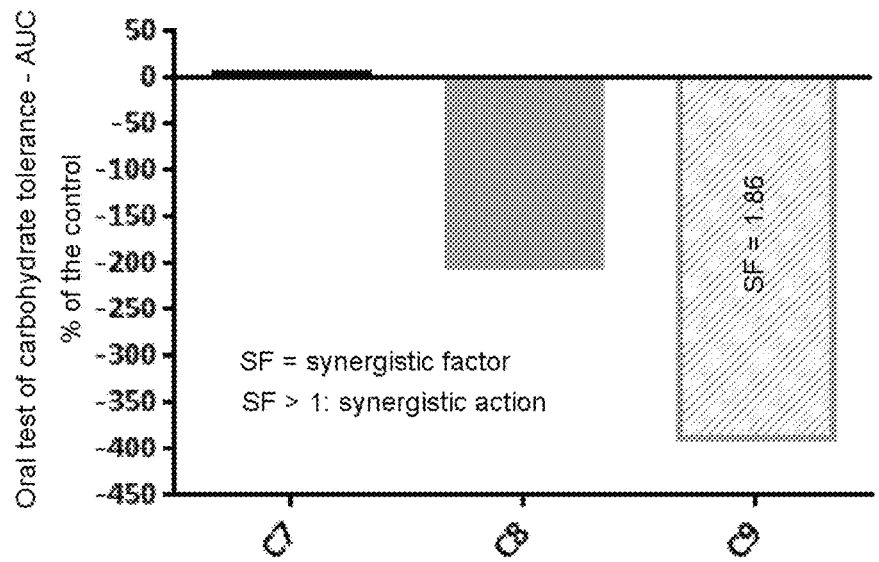
FIG. 5: the results demonstrating the synergistic effect afforded by a composition according to the invention, these results corresponding to the results of table 14 (point II.1) for carbohydrate tolerance.
Figure 6:
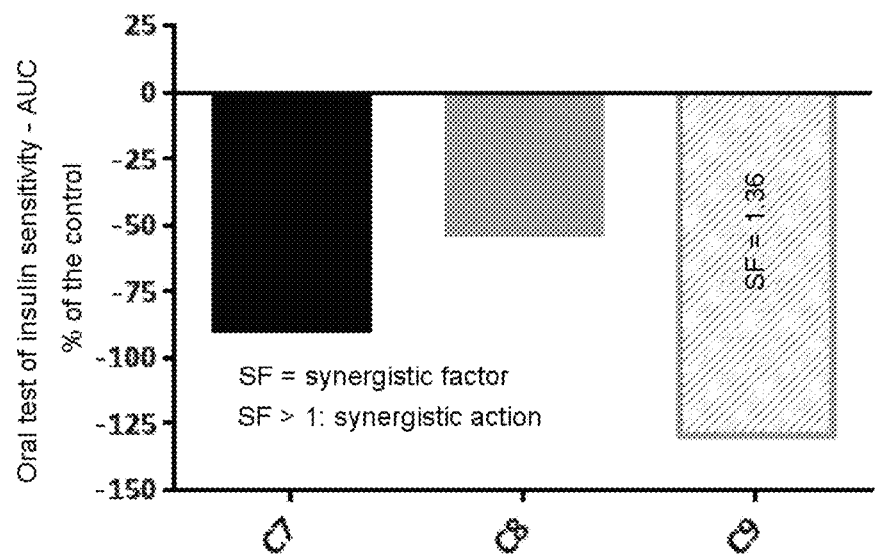
FIG. 6: the results demonstrating the synergistic effect afforded by a composition according to the invention, these results corresponding to the results of table 14 (point II.1) for insulin sensitivity.

The results presented in Table 14 are illustrated in FIGS. 4, 5 and 6. A large synergistic effect with composition C9 according to the invention is demonstrated, on the fasting glycemia, on the carbohydrate tolerance (AUC) and also on the insulin sensitivity (AUC). This is the case even though composition C7 already had a large and significant effect on improving the insulin sensitivity.

II.2 Tests B

Another composition, C10, was developed and tested in vivo: *Chrysanthellum indicum* (aerial part, dry extract)+*Cynara scolymus* (leaves, dry extract)+*Vaccinium myrtillus* (fruits, dry extract)+*Piper nigrum* (fruits, dry extract)+*Olea europaea* (leaves, dry extract).

More precisely, composition C10 was tested in vivo in comparison with metformin, the reference therapeutic molecule in the treatment of type 2 diabetes, on the same model as Tests A (db/db mice). Using this predictive model of diabetic mice and incorporating composition C10 directly into the rodents' feed (1% *Chrysanthellum indicum*, 1% *Cynara scolymus*, 0.1% *Vaccinium myrtillus*, 0.001% *Piper nigrum* and 0.6% *Olea europaea* of the feed), this makes it possible to ensure its "multi-target" efficacy and its large-scale use, since intravenous or intraperitoneal injections are limited to a small number of people, given their mode of administration.

The experimental time was seven weeks with a "run-in" of one week followed by six weeks of supplementation with composition C10. The male mice were six weeks old at the start of the treatment. The evaluations were made just before the supplementation (t=0), weekly for certain parameters, and at the end of supplementation (t=6 weeks).

The experimental evaluations related especially to:
Measurement of the feed intake (t1, t2, t3, t4 and t5 weeks);
Measurement of the body mass (t0, t1, t2, t3, t4, t5, t6 weeks);
Measurement of the fat mass and lean mass by MRI (magnetic resonance imaging; t0 and t6 weeks);
Measurement of the fasting glycemia (t0, t1, t2, t3, t4, t5, t6 weeks);
Measurement of the glycated hemoglobin (HbA1c; t6 weeks);
The insulin sensitivity (test identical to that performed in Tests A; t0 and t6 weeks);
The carbohydrate tolerance (test identical to that performed in Tests A; t0 and t6 weeks);
Measurement of the hepatic and serum triglycerides (t6 weeks);
Measurement of the serum HDL cholesterol (t6 weeks).

These evaluations are all entirely familiar to a person skilled in the art.

The results are presented in Table 15 below. It is important to consider that the amount of metformin ingested daily by the mice was about 26% greater than the total amount of molecules present in composition C10 according to the invention. In other words, the dose of metformin administered was greater than the dose of total molecules present in composition C10.

| Parameters | Control | Metformin | C10 |
|---|---|---|---|
| Feed intake (g/day) | 9.6 ± 0.5 | 10.0 ± 0.6 | 10.7 ± 0.8 |
| Body mass (g) | 44.7 ± 2.0 | 40.8 ± 2.1 | 36.3 ± 1.7 [a] |
| Fat mass (%) | 26.1 ± 1.5 | 23.2 ± 1.7 | 19.1 ± 1.1 [a] |
| Lean mass (%) | 17.0 ± 0.5 | 16.5 ± 0.5 | 16.5 ± 0.6 |
| Fasting glycemia (mg/dL) | 437 ± 26 | 474 ± 24 | 160 ± 20 [a, b] |
| HbA1c (%) | 8.33 ± 0.53 | 7.59 ± 0.24 | 4.25 ± 0.20 [a, b] |
| Area under the curve measured during an oral test of insulin sensitivity (AUC, mg · min/dL) | 50940 ± 2968 | 32778 ± 3166 | 14109 ± 1856 [a, b] |
| Area under the curve measured during an oral test of carbohydrate tolerance (AUC, mg · min/dL) | 61050 ± 2757 | 65614 ± 1577 | 28823 ± 5333 [a, b] |
| Serum triglycerides (mg/dL) | 231.23 ± 18.29 | 256.23 ± 28.19 | 177.80 ± 19.60 [b] |
| Hepatic triglycerides (μmol/mg tissue) | 41.10 ± 1.80 | 38.39 ± 4.84 | 21.39 ± 2.21 [a, b] |
| HDL cholesterol (mg/dL) | 74.34 ± 4.10 | 99.21 ± 6.03 | 111.72 ± 8.39 [a] |

Mean values ± SEM.
Control, n = 10; Metformin, n = 11; C10, n = 10.
Student's t test for unpaired data.
[a] C10 versus control, p < 0.05.
[b] C10 versus Metformin, p < 0.05.

Figure 7:
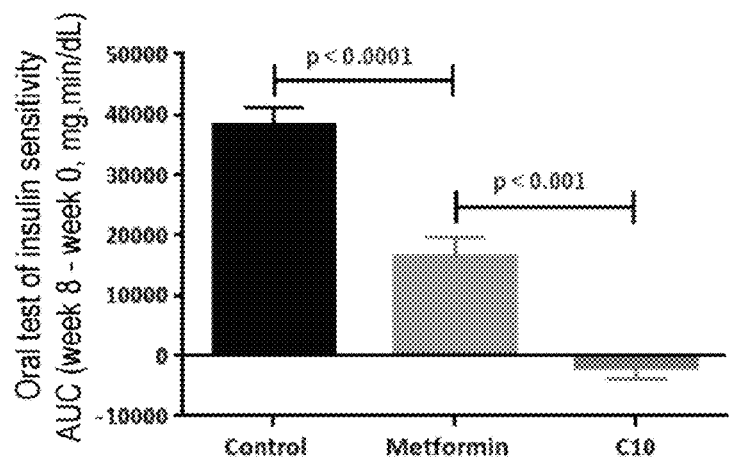
FIG. 7: the results for the effect of a composition according to the invention and metformin, on insulin sensitivity, these results corresponding to the results of table 15 (point II.2)

FIG. 7 more particularly illustrates the effects of metformin and of composition C12 according to the invention on the insulin sensitivity.

The results illustrated in Table 15 show an extremely large and surprising effect of composition C10 according to the invention on a set of risk factors of metabolic syndrome, of excess weight, of obesity, of diabetes, of non-alcoholic steatohepatitis (NASH), and of cardiovascular diseases, namely:

The decrease in body weight via a reduction in the fat mass, without affecting the lean mass;
A decrease in the fasting glycemia and in the glycated hemoglobin;
An improvement in the carbohydrate tolerance;
An improvement in the insulin sensitivity;
A decrease in the hepatic and serum triglycerides;
An increase in the HDL cholesterol ("good cholesterol").

Not only does the composition according to the invention decrease a whole set of risk factors, but above all it improves them to a level virtually equivalent to that of non-diabetic mice (healthy mice). In other words, the invention prevents the installation and progression of type 2 diabetes.

Figure 8:
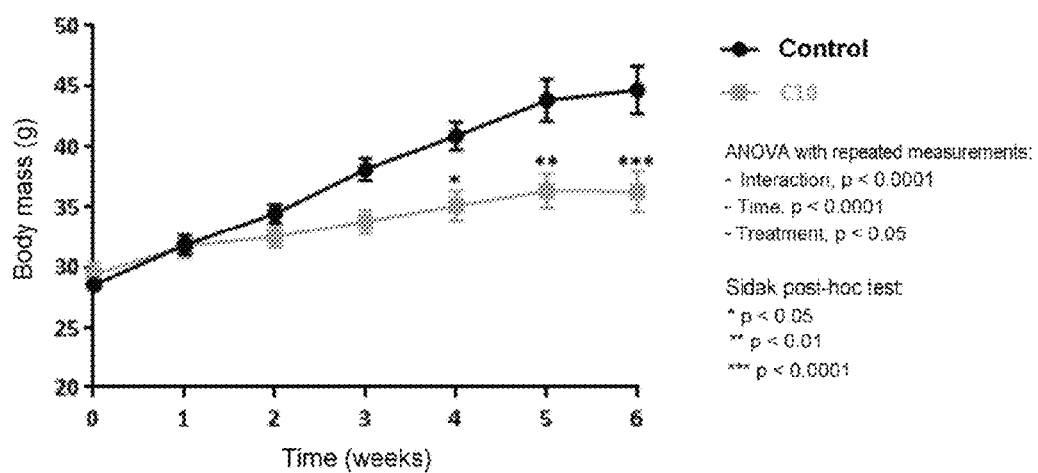
FIG. 8: the results for the effect of a composition according to the invention on the change in body mass, these results corresponding to the results of table 15 (point 11.2)
Figure 9:
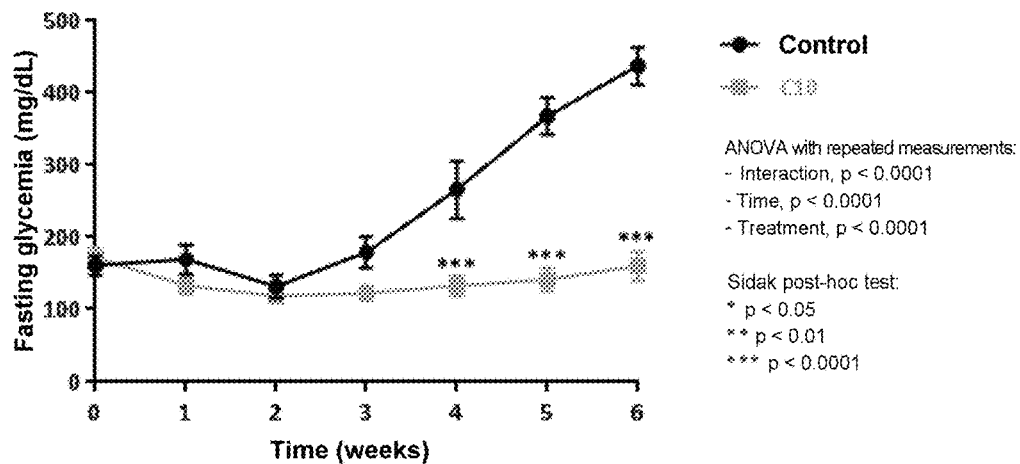
FIG. 9: the results for the effect of a composition according to the invention on the change in fasting glycemia, these results corresponding to the results of table 15 (point II.2)

FIGS. 8 and 9 illustrate the effects of composition C10 according to the invention on the change in body mass and in fasting glycemia compared with the control group. Composition C10 according to the invention substantially limits a gain in mass and prevents an increase in glycemia.

Furthermore, its effects are very much superior to those of metformin, the main antidiabetic medicament (Ferrannini E et al. Eur Heart J 2015; Jun. 10; example: GLU-COPHAGE®) and demonstrates the absence of side effects on the circulating fats, in contrast with OCA (obeticholic acid, an FXR agonist intended for treating type 2 diabetes and NASH (non-alcoholic steatohepatitis)) developed by the company INTERCEPT, which drastically reduces the circulating HDL cholesterol ("good cholesterol") (−0.2 g/L, $p<0.01$). Quite to the contrary, the composition according to the invention increases the level of HDL cholesterol by 50.3%.

Moreover, the effect of the composition according to the invention is greater than that of the candidate medicament developed by the company GENFIT, GFT 505 (Elafibranor), on glycated hemoglobin (HbA1c), the main diagnostic indicator of type 2 diabetes and of its morbid complications: composition C10, HbA1c=4% versus GFT 505, HbA1c=6% for the highest dose (same model of db/db mice and similar experimental design; Hanf R et al. Diab Vasc Dis Res 2014; 11:440-7). A further 1% decrease in HbA1c reduces the risks of infarction by 14%, of cardiovascular diseases by 37%, and of amputations by 43%.

Moreover, the composition according to the invention retards, or even stops, the degeneration of the pancreatic beta cells, which are the cells responsible for insulin secretion in response to an increase in glycemia. Specifically, type 2 diabetes gradually induces a degradation of the pancreatic beta cells partly associated with chronic hyperglycemia. This is reflected by an increase in insulin secretion in the first stages of the disease to reduce the glycemia (increase in insulinemia), followed by a gradual decrease in its secretion (lower circulating insulinemia) due to the gradual destruction of the beta cells (Leahy J L et al. J Clin Invest 1985; 77:908-915). The results obtained strongly support an effect of composition C10 on the pancreatic beta cells. Specifically, after six weeks of supplementation, the insulinemia is higher in the composition C10 group according to the invention versus control ($27.40\pm4.11$ versus $9.64\pm2.53$ ng/mL, $p<0.01$, respectively), reflecting a very different stage of advancement of the diabetes: advanced diabetes in the Control group with destruction of the beta cells (low insulinemia, high fasting glycemia, high HbA1c) and sparingly advanced diabetes or even no diabetes in the group of composition C10 according to the invention with functional beta cells (high insulinemia, low glycemia, low HbA1c).

Thus, the invention fully satisfies the need for novel preventive solutions and therapeutic solutions taking into account the multifactor nature of cardio-metabolic disorders. This invention represents a major advance for considerably eradicating the development of metabolic diseases and their morbid nature.

Molecular biology measurements on the liver were also taken. These evaluations were performed after the six weeks of treatment and after sacrificing the animals. In particular, the amounts of hepatic AMPK (AMP-activated protein kinase) proteins were determined by western blotting. AMPK is considered as being a metabolic sensor. AMPK, a ubiquitous enzyme, participates in the coordinated regulation of energy metabolism, food intake and the sensitivity of tissues in response to numerous metabolic and hormonal signals. These properties thus give it a role as a major pharmacological target with metabolic applications (diabetes, insulin resistance, obesity) and cardiological applications (cardiac ischemia, diabetes-related complications) (Coughlan K A et al. Diabetes Metab Syndr Obes 2014; 7:241-53). Increasing the amounts of AMPK constitutes a strategy of primary interest in the identification and validation of treatments for type 2 diabetes and its complications (especially non-alcoholic steatohepatitis), and more globally for pathologies related to metabolic disorders.

Figure 10:
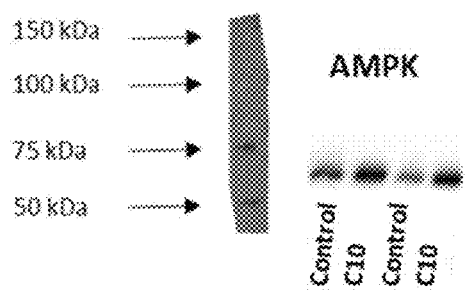
FIG. 10: the results of western blotting showing an increase in the amount of AMPK in mouse liver with a composition according to the invention (point II.2)

The results show in the liver that composition C10 according to the invention induces a marked increase in the amount of AMPK (control n=9, $1.00\pm0.22$ versus C10 n=9, $1.96\pm0.73$, $p<0.001$, Mann Whitney Test U). The results are illustrated by the western blot FIG. 10.

The experimental protocol that may be performed by any person skilled in the art is indicated in the lines below.

→ AMPK

Protein Extraction 50 mg of frozen tissue (liver) were placed in 20 volumes of NP-40 buffer (50 mM Tris HCl, pH: 7.4, 150 mM NaCl, 1 mM NaF, 1 mM Na3VO4, 1% Nonidet P-40, 0.25% sodium deoxycholate) in the presence of 1 µL of protease inhibitor cocktail (P8340, Sigma-Aldrich) and phosphatase-inhibiting tablets (#88667 Thermo Fisher Scientific, USA). The tissues were homogenized in ice using a glass Potter grinder and then centrifuged at 14 000 g for 10 minutes at 4° C. before recovering the supernatent. The protein content of the supernatent was assayed with a Bio-Rad DC kit (Bio-Rad, USA) and then all the samples were brought to the same standard concentration before being diluted a second time in Laemmli 2× buffer and then heated at 90° C. for 3 minutes.

Blotting

For each test, a molecular weight scale and an internal control were deposited next to 15 µg of each sample on a polyacrylamide gradient gel (4-15% Mini-PROTEAN® TGX Stain-Free™ Gel, BioRad, USA). The gels were then subjected to a current of 300 V for 18 to 20 minutes in an electrophoresis buffer (25 mM Tris, 192 mM glycine, 0.1% SDS) before transferring the proteins onto PVDF membrane by means of a semi-liquid transfer system (Transblot, Bio-Rad, USA) with a direct current of 25 V and 2.5 A for 7 minutes. The membranes were then incubated in a Tween-Tris saline buffer (TTBS: 50 mM Tris base pH: 7.5, 150 mM NaCl, and 0.01% Tween 20) enriched with 5% of BSA for 1 hour at room temperature. The membranes were then rinsed with TTBS and then incubated overnight at 4° C. with anti-AMPKα antibodies (D63G4, Cell Signaling, USA).

After the incubation, the membranes were washed again with TTBS and then exposed to an anti-rabbit secondary antibody conjugated to horseradish peroxidase, at a concentration of $1:3000^{th}$ for one hour at room temperature. The membranes were then washed three times in TTBS before being exposed to a chemiluminescence solution (Clarity Western ECL; Bio-Rad, USA) for one minute. The membranes were then scanned on a Bio-Rad Chemidoc system and the intensity of the bands measured using the supplied image analysis software (ImageLab V4.1, Bio-Rad, USA).

II.3 Test C

Figure 11:
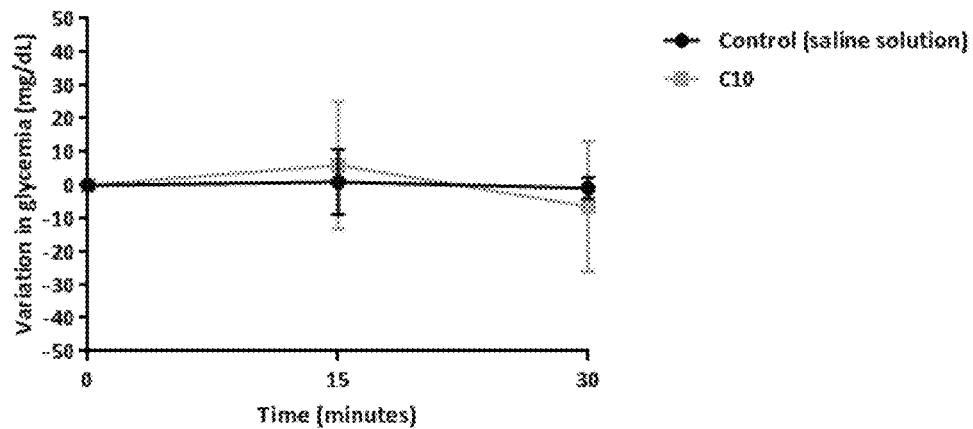
FIG. 11: the results of tests showing the absence of an acute hypoglycemiant effect with a composition according to the invention (point II.3)

One of the main drawbacks of many therapeutic molecules currently on the market is their acute hypoglycemiant effect, with a high risk of hypoglycemia. To test the acute hypoglycemiant effect of composition C10 according to the invention, the composition was administered by force-feeding (400 mg/kg) to six healthy C57BL/6N mice. The glycemia was measured by biopsy in the tail before and after force-feeding (t0, t15 minutes, t30 minutes). Moreover, according to a crossed protocol, the same mice received by force-feeding a saline solution with glycemia measurements (t0, t15 minutes, t30 minutes). The results illustrated in FIG. 11 demonstrate the absence of acute hypoglycemiant effect of composition C10 according to the invention.

II.4 Test D

A composition C11 of a single extract (aqueous-alcoholic dry extract) obtained from powder of *Chrysanthellum indicum* aerial parts, of *Cynara scolymus* leaves, of *Vaccinium myrtillus* fruit, of *Piper nigrum* fruit and of *Olea europaea* leaves (ratio 1/1/0.1/0.0001/0.6) was tested on the same model of diabetic mice used in tests A and B.

The experimental time was 6 weeks with a "run-in" of one week followed by five weeks of supplementation with composition C11. The male mice were six weeks old at the start of the treatment. The evaluation of body mass was performed just before supplementation (t=0), weekly, and at the end of supplementation (t=5 weeks). The composition was incorporated into the rodents' feed at a rate of 2.7% of the food (same amount as composition C10).

Figure 12:
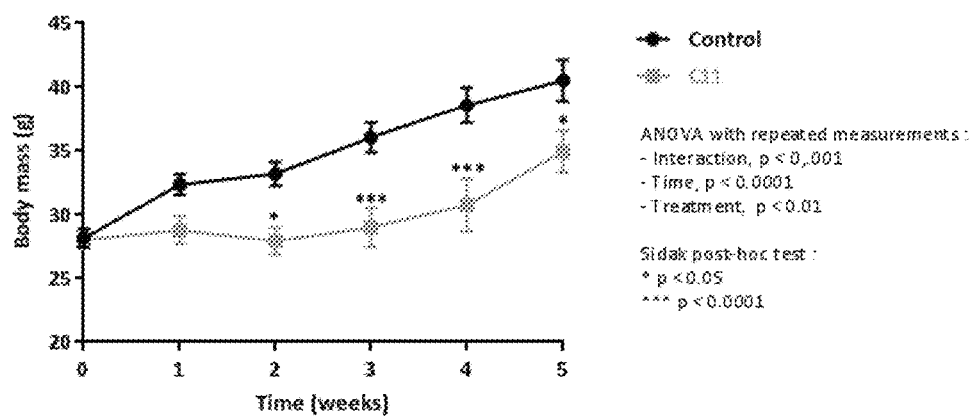
FIG. 12: the results of tests showing the effect of a composition according to the invention on the change in body mass increase (point II.4).

FIG. 12 illustrates the effects of composition C11 according to the invention on the change in body mass compared with the control group. Composition C11 according to the invention greatly limits the gain in body mass.

III. IN VITRO EVALUATION OF THE EFFICACY OF THE COMPOSITION in vitro experiments were also performed to demonstrate the effects of compositions C10 and C11 according to the invention. Composition C12 of combination of molecules according to the invention was also tested: dicaffeoylquinic acid+apigenin 7-O-glucuronide+monocaffeoylquinic acid+ oleuropein+piperine (ratio 1/1/1/1/0.001).

Various enzymatic activity tests were performed in order to determine whether the compositions according to the invention inhibited strategic enzymes of carbohydrate and fat metabolism: Alpha-glucosidase, DPP-IV and HMG-CoA reductase. An action on all of these strategic targets allows global care management of type 2 diabetes and of its complications (diabetic foot, retinopathy, loss of vision, nephropathy, cardiovascular events, non-alcoholic steatohepatitis or NASH).

➔ HMG-CoA Reductase

To control the circulating fats, the objective is to reduce the concentration of serum cholesterol by mainly targeting the inhibition of cholesterol biosynthesis (inhibition of 3-hydroxy-3-methyl-glutaryl-coenzyme A or HMG-CoA reductase). Pravastatin is one of the reference molecules for reducing LDL cholesterol and total cholesterol. It is especially sold under the name ELISOR®, PRAVASTATINE MYLAN, VASTEN®, PRAVASTATINE TEVA.

➔ Alpha-Glucosidase alpha-Glucosidase is an enzyme which catalyzes the final step in the process of digestion of carbohydrates. alpha-Glucosidase inhibitors (examples of medicaments included in this category: GLUCOR®, DIASTABOL®) are used for reducing postprandial glycemia, which is considered as a risk factor independent of the macrovascular complications in diabetes (Kim J S et al. Biosci Biotechnol Biochem 2000; 64:2458-61).

➔ DPP-IV (Dipeptidyl Peptidase-IV)

DPP-IV inhibitors are considered as one of the most promising strategies for the care management of type 2 diabetes (von Geldern T W et al. Drug Development Research 2006; 67:627-42). DPP-IV rapidly deactivates the hormones GLP-1 (glucagon-like peptide 1) and GIP (glucose-dependent insulinotropic polypeptide), also known as incretins. Inhibition of DPP-IV makes it possible especially to increase the action of GLP-1 and of GIP, thus allowing a physiological stimulation of insulin secretion and an inhibition of glucagon secretion by the pancreas, and consequently a decrease in glycemia. Moreover, the inhibition of DPP-IV promotes gastric emptying and brings about a central anorexigenic effect. Inhibition of DPP-IV thus allows better regulation of carbohydrates in the case of diabetic individuals. Clinical studies moreover show that DPP-IV inhibitors have good efficacy with good tolerability in the care management of hyperglycemia in the case of individuals suffering from type 2 diabetes, without weight gain and hypoglycemia phenomena (Green B D et al. Diabetes Vasc Dis Res 2006; 3:159-65). One of the reference inhibitors is diprotin A.

The experimental protocol for evaluating the inhibitory potential of compositions C10, C11 and C12 was as follows:

Preparation of the Extracts, Mixtures of Extracts and Mixture of Pure Synthetic Molecules For the tests of inhibition of HMG-CoA reductase and of glucosidases, the plant extracts were diluted in ultra-pure water/ethanol mixtures, the proportions of which varied according to the type of extract, so as to obtain homogeneous solutions.

After homogenization, the samples were centrifuged at 4000 rpm for 10 minutes and the supernatents were recovered (1-15 Fisher Bioblock Scientif centrifuge, Sigma-Aldrich®). The molecules were diluted either in 90/10 (v/v) ultra-pure water/DMSO or in 50/50 (v/v) ultra-pure water/ethanol.

The mixtures of several plant extracts were diluted in 50/50 (v/v) water/ethanol and were then ultrasonicated for 15 minutes, so as to homogenize the medium (use of a UP50H Hielscher® ultrasonication probe at maximum power). Finally, they were centrifuged at 4000 rpm for 10 minutes and the supernatents were recovered (1-15 Fisher Bioblock Scientif centrifuge, Sigma Aldrich®).

In the case of the DPP-IV test, the samples were diluted either in Trisma-HCl buffer (pH 8.0; 100 mM) or in 90/10 (v/v) ultra-pure water/DMSO.

Test of Inhibition of HMG-CoA Reductase

This test makes it possible to measure, by a decrease in absorption over time, at $\lambda=340$ nm, the efficacy of inhibition of the enzymatic activity. The reaction mechanism is as follows:

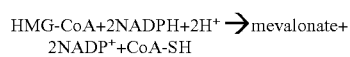

HMG-CoA+2NADPH+2H$^+$ ➔ mevalonate+ 2NADP$^+$+CoA-SH

Disappearance of the substrate NADPH (absorbing at 340 nm) is thus monitored over time. A decrease in the variation of the absorbance at 340 nm over time relative to the control reaction without inhibitor (100% activity) is evidence of inhibition of the enzyme.

In a first stage, the solutions need to be prepared from the Sigma® kit:
- the 5× buffer supplied must be diluted to a concentration of 1× in ultra-pure water;
- the NADPH is dissolved by adding 1× buffer, and then distributed in 100 µL tubes;
- the starting enzyme solution is distributed in 25 µL aliquots.

The buffer and the NADPH were stored at −20° C. and the enzyme aliquots were stored at −80° C. until the time of use.

The manipulations were performed directly in 96-well microplates (NUNC96 or SARSTEDT96). The buffers, substrates, inhibitors and the enzyme were added in a specific order (see below). For each microplate, it was necessary to prepare a blank, a control and various tests were prepared. Each element was prepared in duplicate (or even in triplicate):
- preparation of the blank: 24 µL of the solvent used for the samples, 12 µL of HMG-CoA, 158 µL of 1× buffer, 4 µL of NADPH; incubation at 37° C., 3 to 5 min;
- preparation of the negative control: 24 µL of the solvent used for the samples, 12 µL of HMG-CoA, 158 µL of 1× buffer, 4 µL of NADPH; incubation at 37° C., 3 to 5 min; addition of 2 µL of enzyme;
- preparation of the test: 24 µL of the potentially inhibiting sample, 12 µL of HMG-CoA, 158 µL of 1× buffer, 4 µL of NADPH; incubation at 37° C., 3 to 5 min; addition of 2 µL of enzyme.

After preparing the plate, the kinetic monitoring was performed in a microplate reader (BMG Labtech) over 16 minutes, 25 seconds, with values taken every 25 seconds at λ=340 nm, i.e. a total of 40 cycles. From this, the percentages of inhibition could be calculated.

Test of Inhibition of α-Glucosidases

The α-glucosidase inhibition tests were performed by monitoring by spectrophotometry, at λ=405 nm, the formation of the yellow-colored product para-nitrophenol (PNP) from the synthetic substrate: para-nitrophenyl-α-D-glucopyranoside (PNPg), according to the following hydrolysis reaction, catalyzed by α-glucosidases:

PNPg+H$_2$O → PNP+glucose

A reduction in the variation of the absorbance, at λ=405 nm, over time relative to the control reaction without inhibitor (100% activity) is evidence of inhibition of the enzyme.

The recombinant human enzyme produced in *Saccharomyces cerevisiae* (maltase) (Sigma-Aldrich®, G0660) was diluted in phosphate buffer (0.1 M, pH 6.8) to pass from a stock solution theoretically at 120 U/mL to a solution with an activity of 1.6 U/mL, used for the tests.

During the α-glucosidase inhibition tests, the manipulations were performed directly in 96-well microplates (NUNC96 or SARSTEDT96). The buffers, substrates, inhibitors and the enzyme are added in a specific order (see below). For each microplate prepared, a blank, a control and various tests are prepared. Each element is prepared in duplicate (or even in triplicate):
- preparation of the blank: 100 µL of phosphate buffer (0.1 M, pH 6.8), 20 µL of the solvent used for the samples, incubation at 37° C., 10 to 15 min, followed by addition of 20 µL of PNPg at 2.5 mM (dissolved in phosphate buffer);
- preparation of the negative control: 100 µL of phosphate buffer (0.1 M, pH 6.8), 20 µL of the solvent used for the samples, 20 µL of enzymes at 1.6 U/mL, incubation at 37° C., 10 to 15 min, followed by addition of 20 µL of PNPg at 2.5 mM (dissolved in phosphate buffer);
- preparation of the test: 100 µL of phosphate buffer (0.1 M, pH 6.8), 20 µL of potentially inhibiting sample, 20 µL of enzyme at 1.6 U/mL, incubation at 37° C., 10 to 15 min, followed by addition of 20 µL of PNPg at 2.5 mM (dissolved in phosphate buffer).

After preparation of the plate, the kinetic monitoring was performed in a microplate reader (BMG Labtech) over 30 minutes, with values taken every 2 minutes at λ=405 nm, i.e. a total of 16 cycles. From this, the percentages of inhibition could be calculated.

Test of Inhibition of DPP-IV

The DPP-IV inhibition tests are performed by monitoring by spectrophotometry, at 385 nm, the formation of the product p-nitroaniline from the synthetic substrate: Gly-L-Pro-p-nitroanilide, according to the following hydrolysis reaction catalyzed by DPP-IV:

Gly-L-Pro-p-nitroanilide+H$_2$O → p-nitroaniline+Gly-L-pro

A decrease in the variation of the absorbance at 385 nm over time relative to the control reaction without inhibitor (100% activity) is evidence of inhibition of the enzyme.

The enzyme used was at a concentration of 0.045 U/mL (with U=µmol/min), and it thus needed to be diluted. Since the dilution was large, it was necessary to perform two successive dilutions.

First dilution (production of a solution at 5×10$^{-4}$ U/mL):

$$D1 = \frac{5 \times 10^{-4} * 450}{0.045} = 5 \text{ µL}$$

(Vfinal: 450 µL; V(stock solution of enzyme)=5 µL)

Second dilution (production of a solution at 5×10$^{-6}$ U/mL)

$$D2 = \frac{5 \times 10^{-6} * 1000}{5 \times 10^{-4}} = 10 \text{ µL}$$

(Vfinal: 1000 µL; V(D1)=10 µL)→ solution D2 was the usable solution.

The manipulations were performed directly in 96-well microplates (NUNC96 or SARSTEDT96). The buffers, substrates, inhibitors and the enzyme were added in a specific order (see below). For each microplate prepared, a blank, a control and various tests were performed. Each element was prepared in duplicate (or even in triplicate):
- preparation of the blank: 25 µL of the sample, 25 µL of substrate (Gly-L-pro-p-nitroanilide dissolved in Tris-HCl buffer (100 mM, pH 8.0) at a concentration of 1.6 mM);
- preparation of the negative control: 25 µL of the diluent used for the sample, 25 µL of substrate, incubation at 37° C., 10 min, 50 µL of enzyme at 5×10$^{-6}$ U/mL (prepared in 100 mM TrisHCl buffer, pH 8.0);
- preparation of the test: 25 µL of potentially inhibiting sample, 25 µL of substrate, incubation at 37° C., 10 min, 50 µL of enzyme at 5×10$^{-6}$ U/mL.

After preparation of the plate, the kinetic monitoring was performed in a microplate reader (BMG Labtech) over 30 minutes, with values taken every minute at λ=385 nm, i.e. a total of 31 cycles. From this, the percentages of inhibition could be calculated.

Calculation of the Inhibition Percentages

In general, irrespective of the test, for a given concentration of an inhibitor, a curve of equation: absorbance=f(time) (in minutes) was prepared. Similarly, controls (without inhibitor) and blanks (without enzymes) were systematically prepared.

On the various curves obtained, only the linear parts at the start of kinetics were retained, since they corresponded to the conditions for determining the initial rates. Thus, the slope in absorbance/minute was proportional to the rate of appearance of the product (glucosidase and DPP-IV) or of disappearance of the substrate (HMG-CoA reductase, negative slope).

Depending on the types of tests, the percentages of inhibition of the various enzymes were calculated via various methods:

for the tests for inhibition of HMG-CoA reductase and of α-glucosidases, the calculation formula is identical:

$$\% \text{ inhibition} = \frac{\text{control slope} - \text{sample slope}}{\text{control slope}} * 100.$$

for the test of inhibition of DPP4, the formula is slightly different since blanks are taken into account:

$$\% \text{ inhibition} = \frac{(\text{control slope} - \text{blank slope}) - (\text{control slope} - \text{blank slope})}{(\text{control slope} - \text{blank slope})} * 100.$$

Finally, a mean value of percentage inhibition was calculated for each concentration of inhibitor, and also the standard deviation of each value. If the standard deviation values were greater than 10%, new tests in duplicate were performed, until values of less than 10% were obtained.

The results obtained on the three enzymes for compositions C10 and C11 according to the invention are summarized in Table 16 below.

| | IC 50 [a] (µg/mL in well) | % of inhibition | |
|---|---|---|---|
| Product | Alpha-glucosidase (Human recombinant Saccharomyces Cerevisiae) | DPP-IV [b] (DPP-IV human recombinant expressed in SF9 cells) | HMG-CoA reductase [c] (Catalytic domain of the human enzyme – recombinant GST fusion protein expressed in E. Coli) |
| Acarbose | 86.3 | Absence of inhibition | Absence of inhibition |
| Diprotin A | Absence of inhibition | 100% | Absence of inhibition |
| Pravastatin | Absence of inhibition | Absence of inhibition | 100% |
| Composition C10 | 4.3 | 15.3% | 48.5% |
| Composition C11 | 4.9 | 29.3% | 32.5% |

[a] IC 50: inhibitory concentration for which the enzyme has only 50% of its activity.
[b] Concentration of sample set at 1.25 mg/mL.
[c] Concentration of sample set at 60 µg/mL.

The results obtained on the three enzymes for the combination of molecules (composition C12 according to the invention) are summarized in Table 17 below.

| | IC 50 [a] (µg/mL in well) | % of inhibition | |
|---|---|---|---|
| Product | Alpha-glucosidase (Human recombinant Saccharomyces Cerevisiae) | DPP-IV [b] (DPP-IV human recombinant expressed in SF9 cells) | HMG-CoA reductase [c] (Catalytic domain of the human enzyme – recombinant GST fusion protein expressed in E. Coli) |
| Acarbose | 86.3 | Absence of inhibition | Absence of inhibition |
| Diprotin A | Absence of inhibition | 89.3% | Absence of inhibition |
| Pravastatin | Absence of inhibition | Absence of inhibition | 100 |
| Composition C12 | 19.7 | 10.3% | 30.1% |

[a] IC 50: inhibitory concentration for which the enzyme has only 50% of its activity.
[b] Concentration of sample set at 250 µg/mL.
[c] Concentration of sample set at 60 µg/mL.

It is found that, in contrast with the reference inhibitory molecules for each enzyme [acarbose (medicament), diprotin A (reference inhibitor), pravastatin (medicament) respectively], compositions C10, C11 and C12 according to the invention are, surprisingly, the only ones to inhibit the three enzymes.

By acting simultaneously on several regulation processes, the compositions according to the invention represent an advantageous preventive means and therapeutic means for preventing and treating diabetes, dyslipidemias and complications thereof. The current therapeutic strategies consist in combining several medicaments in order to reduce the various risk factors individually. Nevertheless, the drug combination may occasionally give rise to serious side reactions, for instance the simultaneous administration of fibrates and statins which increases the risk of myopathy (Denke M A J Manag Care Pharm 2003; 9:17-9). There is therefore at the present time a real need for preventive solutions and medicaments whose "multi-target" mechanism of action has advantages in terms of compliance, tolerance and efficacy. Thus, the compositions according to the invention make it possible to reduce the risk of cardiovascular diseases and to prevent and treat each dysfunction and/or its consequences taken independently.

What is claimed is:

1. A composition in the form of tablets, wafer capsules, gel capsules, sticks, sachets, vials, droppers or in injectable form, the composition contains a mixture of:
   an extract of *Chrysanthellum indicum*,
   an extract of *Cynara scolymus*,
   an extract of *Vaccinium myrtillus*,
   an extract of *Olea europaea*, and
   piperine selected from the group consisting of synthetic piperine and/or an extract of *Piper* containing piperine; and
wherein the composition comprises:
   at least one molecule selected from apigenin 7-O-glucuronide, chrysanthellin A, chrysanthellin B, caffeic acid, luteolin, maritimetin, eriodictyol, isookanin, apigenin, luteolin 7-O-glucoside, maritimein, marein, eriodictyol 7-O-glucoside, flavomarein, apigenin 8-C-

α-L-arabinoside-6-C-β-D-glucoside (shaftoside), apigenin 6,8-C-di-β-D-glucopyranoside (vicenin-2), or analogs thereof,
at least one molecule selected from a dicaffeoylquinic acid, a sulfo-monocaffeoylquinic acid, luteolin, luteolin 7-O-glucoside, luteolin 7-O-glucuronide, apigenin 7-O-glucoside, cynaropicrin, or analogs thereof,
at least one molecule selected from a monocaffeoylquinic acid, delphinidin 3-galactoside, delphinidin 3-glucoside, cyanidin 3-galactoside, delphinidin 3-arabinoside, cyanidin 3-glucoside, petunidin 3-galactoside, cyanidin 3-arabinoside, petunidin 3-glucoside, peonidin 3-galactoside, petunidin 3-arabinoside, peonidin 3-glucoside, malvidin 3-galactoside, malvidin 3-glucoside, malvidin 3-arabinoside, or analogs thereof;
wherein the composition further comprises at least one molecule selected from oleuropein, hydroxytyrosol, and analogs thereof.

2. The composition of claim 1, wherein the *Piper* is chosen from *Piper nigrum*, *Piper aduncum* and *Piper longum*.

3. The composition of claim 1, wherein the extract of *Chrysanthellum indicum* is obtained from *Chrysanthellum indicum* whole plant and/or aerial parts.

4. The composition of claim 1, wherein the extract of *Cynara scolymus* is obtained from *Cynara scolymus* whole plant and/or leaves.

5. The composition of claim 1, wherein the extract of *Vaccinium myrtillus* is obtained from *Vaccinium myrtillus* whole plant and/or fruit.

6. The composition of claim 1, wherein the composition has at least one of the following characteristics:
the composition comprises an effective amount of extract of *Chrysanthellum indicum* allowing the administration of at least 0.00001 g of extract of *Chrysanthellum indicum* per one kg of body weight of the person to whom the composition is administered and per day,
the composition comprises an effective amount of extract of *Cynara scolymus* allowing the administration of at least 0.00001 g of extract of *Cynara scolymus* per one kg of body weight of the person to whom the composition is administered and per day,
the composition comprises an effective amount of extract of *Vaccinium myrtillus* allowing the administration of at least 0.00001 g of extract of *Vaccinium myrtillus* per one kg of body weight and per day,
the composition comprises an effective amount of piperine allowing the administration of at least 0.001 mg of piperine per one kg of body weight of the person to whom the composition is administered and per day, and
the composition comprises an effective amount of single extract corresponding to an administration of at least 0.00001 g of single extract per one kg of body weight of the person to whom the composition is administered and per day.

7. The composition of claim 1, wherein the composition comprises an effective amount of extract of *Olea europaea* allowing the administration of at least 0.00001 g of extract of *Olea europaea* per one kg of body weight of the person to whom the composition is administered and per day.

8. The composition of claim 1, wherein the composition also comprises at least one additional element added to the mixture of molecules, said additional element being chosen from:
the following vitamins: B1, B2, B3, B5, B6, B8, B9, B12 C, A, D, E, K1 and K2;
the following compounds: obeticholic acid, corosolic acid, polyunsaturated fatty acids of the omega 6 and/or omega 3 family, orotic acid, pangamic acid, para-aminobenzoic acid, amygdalin, beta-glucans, carnitine, dimethylglycine, imeglimin, isoflavones, L-arginine, oxytocin, pectin, pyridoxamine, resveratrol, viniferin, L-citrulline;
the following trace elements and minerals: arsenic, boron, calcium, copper, iron, fluorine, iodine, lithium, manganese, magnesium, molybdenum, nickel, phosphorus, selenium, vanadium, zinc;
the following microconstituents of non-essential nature: conjugated linolenic acid, lipoic acid, carotenoids, carnitine, choline, coenzyme Q10, phytosterols, polyphenols of the tannin and lignan family, taurine;
fructo-oligosaccharides, galacto-oligosaccharides;
lactic acid-fermenting bacteria;
yeasts;
mushroom;
products derived from insects that are compatible with the food and pharmaceutical sector;
marijuana and haschisch;
the following coating agents: hypromellose, microcrystalline cellulose, stearic acid, talc, sucrose, shellac, povidone, beeswax;
the following flavors: natural flavor of blueberry or natural flavor of strawberry;
the following acidifying agents: malic acid;
the following antiagglomerating agents: silicon dioxide or magnesium stearate;
the following thickeners: xanthan gum, colloidal silica, fatty acid mono- and diglycerides;
the following stabilizer: calcium phosphate;
the following emulsifier: soybean lecithin;
the following filler: corn starch;
excipients selected from the group consisting of: microcrystalline cellulose, magnesium stearate and dicalcium phosphate.

9. The composition of claim 1, wherein the composition is in the form of a powder, gel, emulsion, or in liquid form.

10. The composition of claim 1, wherein the composition is formulated as a nutrition product and/or medicament for treating pathological disorders of carbohydrate and/or fat metabolism in humans or animals.

11. A method of treatment for a pathological disorder in human and animal patients, the method comprising administering to the patient the composition of claim 1.

12. A method of treating type 1 and type 2 diabetes and/or non-alcoholic fatty liver diseases and/or cardiovascular pathologies and/or pathologies associated with insulin resistance in a patient, the method comprising administering to patient, the composition of claim 1.

13. The method of claim 12, wherein the non-alcoholic fatty liver disease is non-alcoholic steatohepatitis.

14. The method of claim 12, wherein the cardiovascular pathologies are coronary cardiopathies, cerebrovascular diseases, peripheral arteriopathies, and deep vein thromboses.

15. The method of claim 12, wherein the method further comprises administering at least one antidiabetic therapeutic agent chosen from biguanides including metformin, dipeptidyl peptidase-IV (DPP-IV) inhibitors, glucagon-like peptide-1 (GLP-1) analogs, thiazolidinediones (TZDs), sulfonylureas, rapid and slow insulins, sodium glucose co-transporter-2 (SGLT2) inhibitors, glycosidase inhibitors molecules of the fibranor family, or molecules targeting the nuclear receptors and the ROR ($\alpha$, $\beta$, $\gamma$) receptors and Rev-Erb ($\alpha$, $\beta$) receptors.

16. The method of claim 11, wherein the pathological disorder is dyslipidemia.

17. The method of claim 12, wherein the method further comprises administering a hypolipemiant therapeutic agent chosen from: statins, fibrates, nicotinic acid, ion-exchange resins, cholesterol absorption inhibitors, omega 3 polyunsaturated fatty acids, tiadenol, and FXR (Farnesoid X Receptor) nuclear receptor agonists.

18. The method of claim 11, wherein the pathological disorder is obesity and excess weight and/or metabolic syndrome and/or pathological problems of arterial tension.

19. The method of claim 15, wherein the glycosidase inhibitors are selected from the group consisting of acarbose, miglitol, voglibose, and peptides containing the alanine-proline or proline-alanine sequence.

20. The method of claim 15, wherein the fibranor family is elafibranor.

\* \* \* \* \*